United States Patent
Van Voorst et al.

(10) Patent No.: US 10,625,094 B2
(45) Date of Patent: Apr. 21, 2020

(54) HEAD RESTRAINT SYSTEM

(71) Applicant: Medtec, Inc., Orange City, IA (US)

(72) Inventors: Keith Alan Van Voorst, Hull, IA (US); Travis Scott De Jong, Orange City, IA (US)

(73) Assignee: Medtec, Inc., Orange City, IA (US)

( * ) Notice: Subject to any disclaimer, the term of this patent is extended or adjusted under 35 U.S.C. 154(b) by 384 days.

(21) Appl. No.: 15/639,480

(22) Filed: Jun. 30, 2017

(65) Prior Publication Data

US 2018/0008840 A1  Jan. 11, 2018

Related U.S. Application Data

(60) Provisional application No. 62/358,327, filed on Jul. 5, 2016.

(51) Int. Cl.
*A61N 5/10* (2006.01)
*A61F 5/37* (2006.01)

(52) U.S. Cl.
CPC .............. *A61N 5/10* (2013.01); *A61F 5/3707* (2013.01); *A61F 5/3769* (2013.01); *A61N 5/1049* (2013.01); *A61N 2005/1087* (2013.01); *A61N 2005/1097* (2013.01)

(58) Field of Classification Search
CPC .... A61F 5/3776; A61F 5/3715; A61F 5/3723; A61F 5/055; A61G 13/121; A61G 13/1235; A61G 7/072; A61G 13/1265; E05B 75/00; A61B 90/18; A61B 2034/2055; A61B 2090/103
See application file for complete search history.

(56) References Cited

U.S. PATENT DOCUMENTS

| | | | |
|---|---|---|---|
| 5,848,449 A * | 12/1998 | Hauger | A61B 6/0421 5/637 |
| 6,138,302 A | 10/2000 | Sashin et al. | |
| 6,698,045 B1 | 3/2004 | Coppens et al. | |
| 2005/0229936 A1 | 10/2005 | Ungemach et al. | |
| 2007/0189461 A1 | 8/2007 | Sommer | |
| 2010/0000549 A1 | 7/2010 | Nieberding | |
| 2012/0085356 A1* | 4/2012 | Whitmore, III | A61F 5/3769 128/870 |
| 2015/0335463 A1 | 11/2015 | De Gruytere | |

OTHER PUBLICATIONS

International Search Report and Written Opinion issued in corresponding International Application No. PCT/US2017/040342, dated Sep. 28, 2017, 13 pages.

(Continued)

*Primary Examiner* — Ophelia A Hawthorne
(74) *Attorney, Agent, or Firm* — Snyder, Clark, Lesch & Chung, LLP

(57) ABSTRACT

A restraint system for a patient to be exposed to a radiation beam is disclosed. The system includes a patient support panel and a head restraint assembly in the form of a face mask to which plural clips are secured. The patient support panel includes plural connectors, which may include fixed or adjustable connectors. The clips include are configured to engage the plural connectors in a snap-on manner, without the need for tools or separate fastening devices.

19 Claims, 13 Drawing Sheets

(56) References Cited

OTHER PUBLICATIONS

Qfix. Positioning patients for life. Radiotherapy Patient Positioning & Immobilization: BoS Headframe. Retrieved online: http://www.qfix.com/qfix-products/proton.asp?CID=7&PLID=75, print date: Aug. 1, 2017, 5 pages.

Qfix. Positioning patients for life. Radiotherapy Patient Positioning & Immobilization: Positioning patients for life. Retrieved online: http://www.qfix.com/index.asp, print date Aug. 1, 2017, 1 page.

* cited by examiner

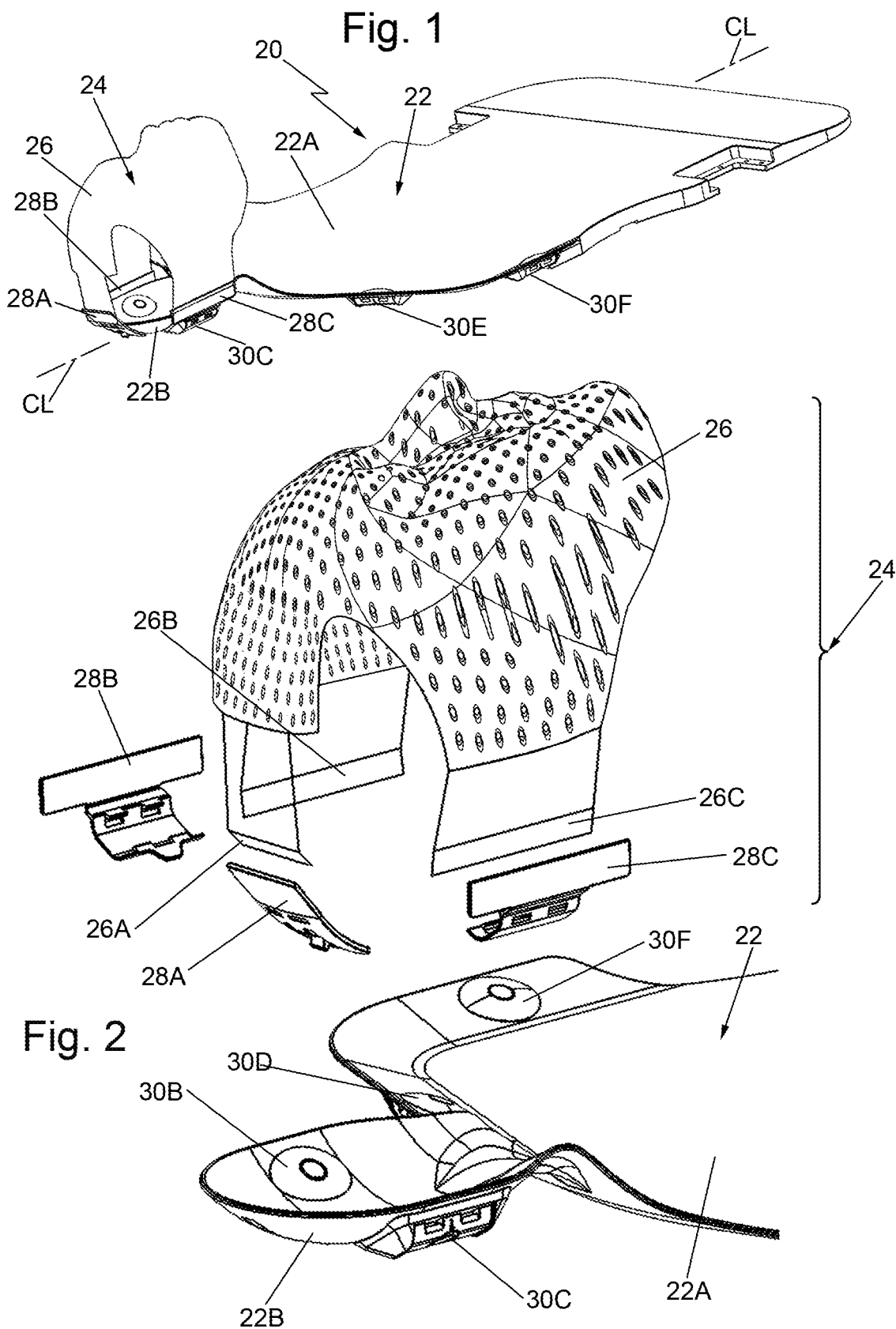

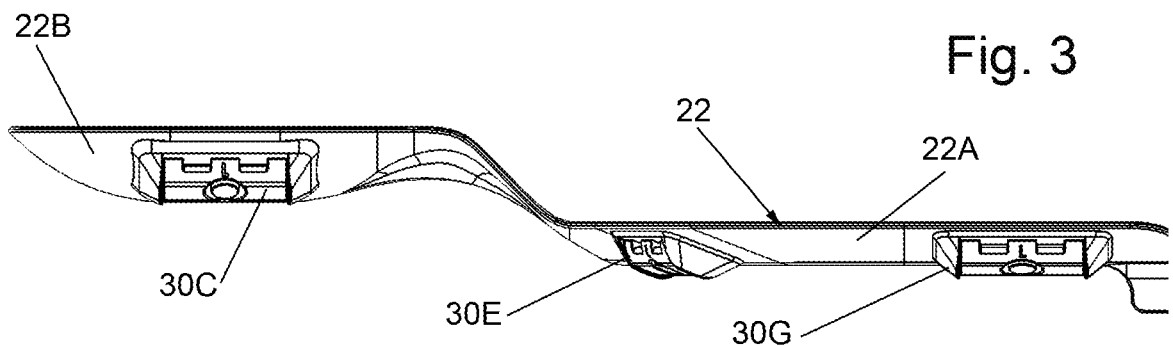
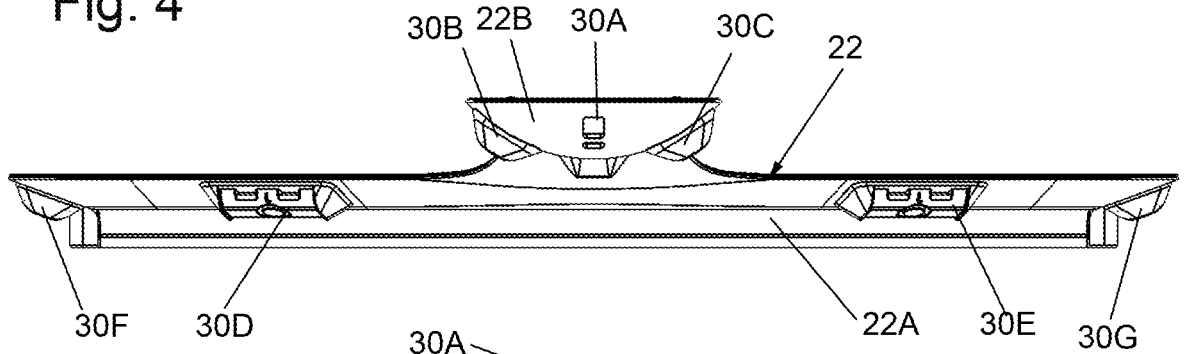
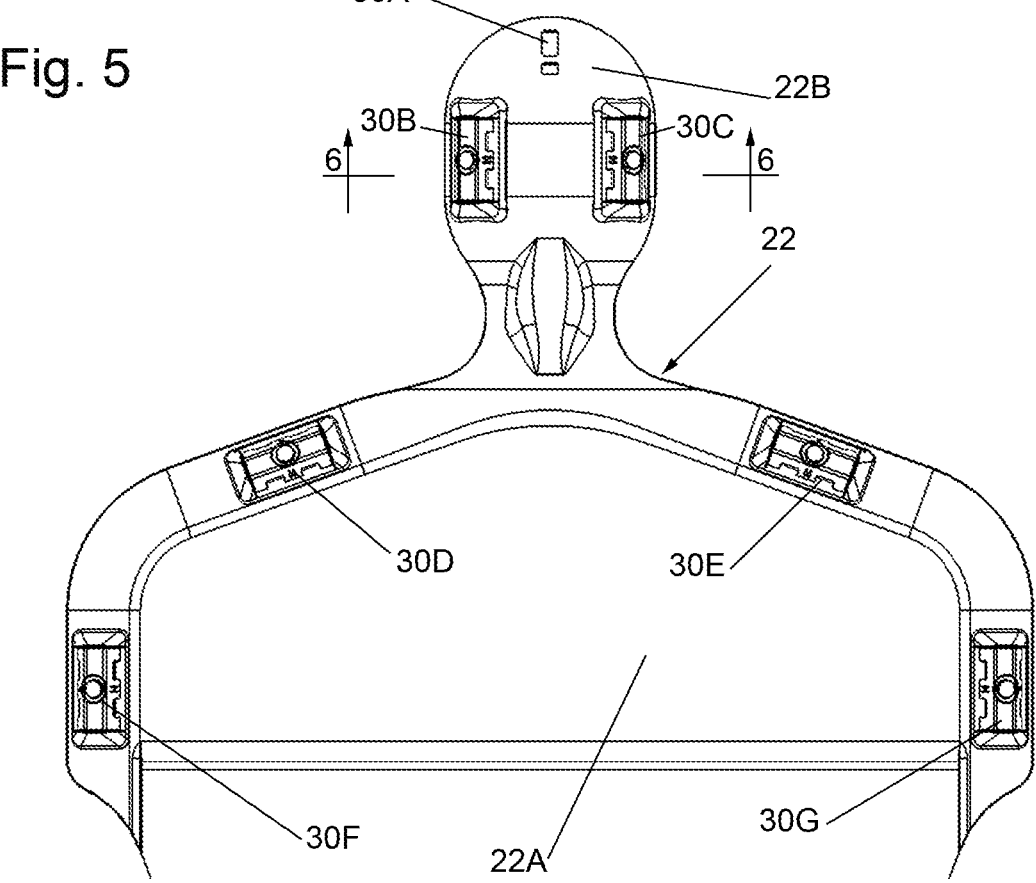

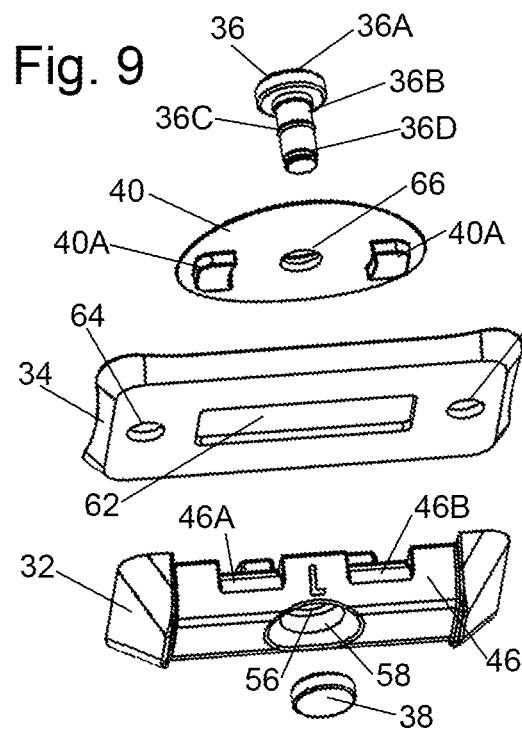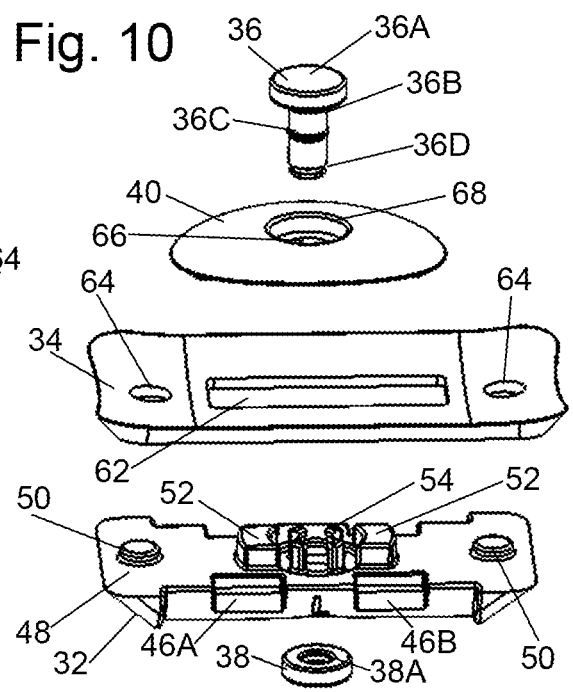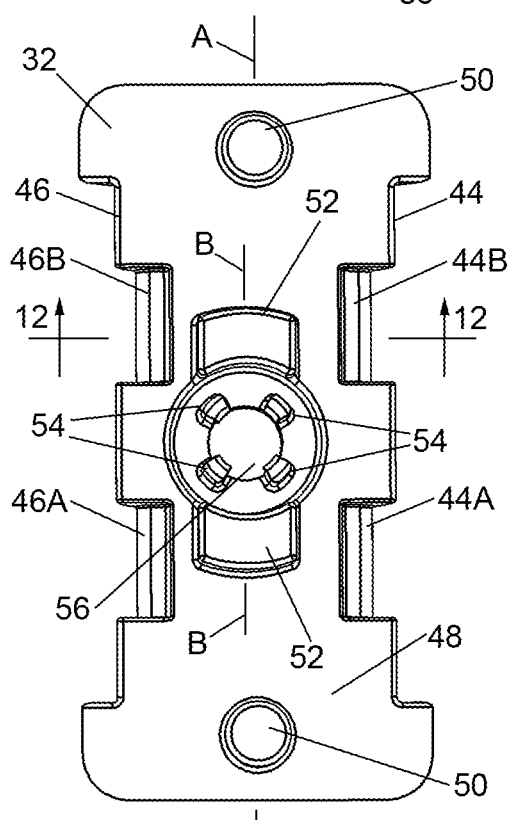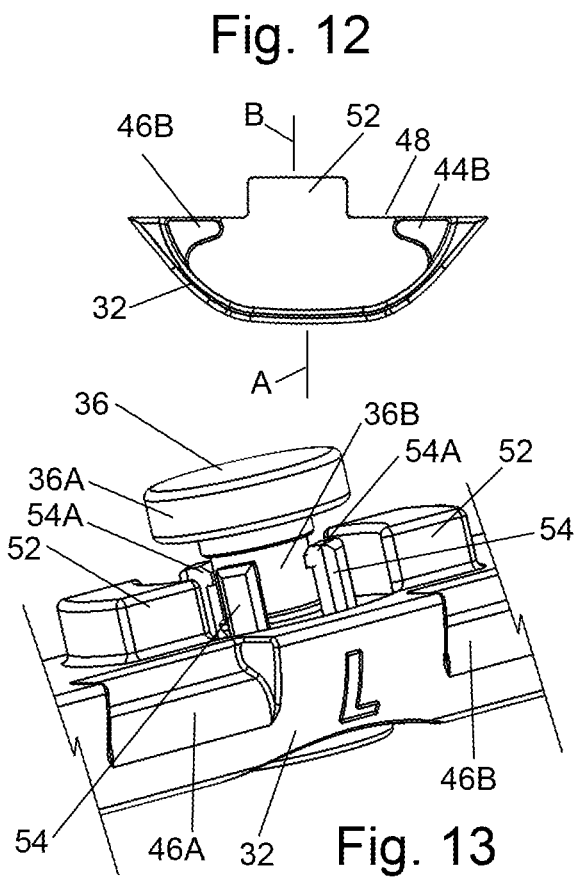

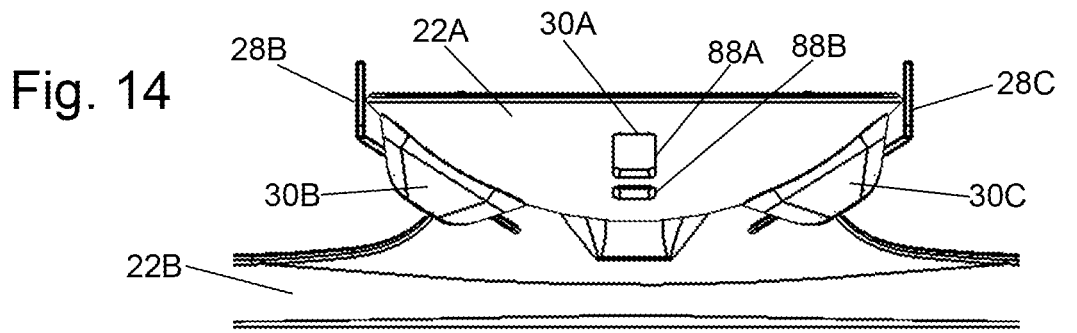
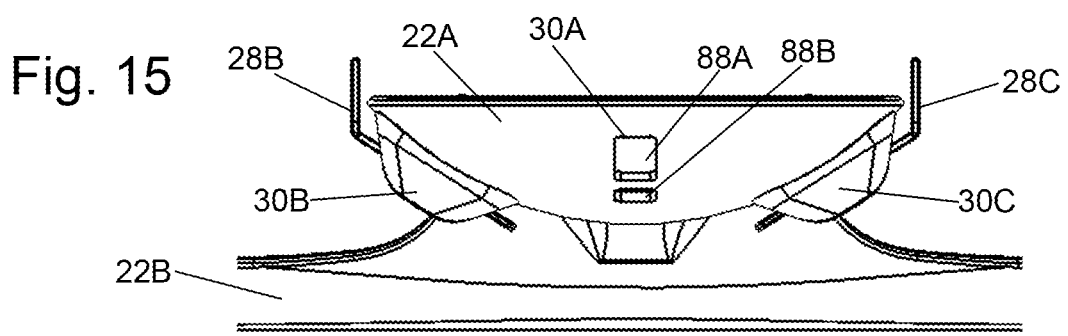
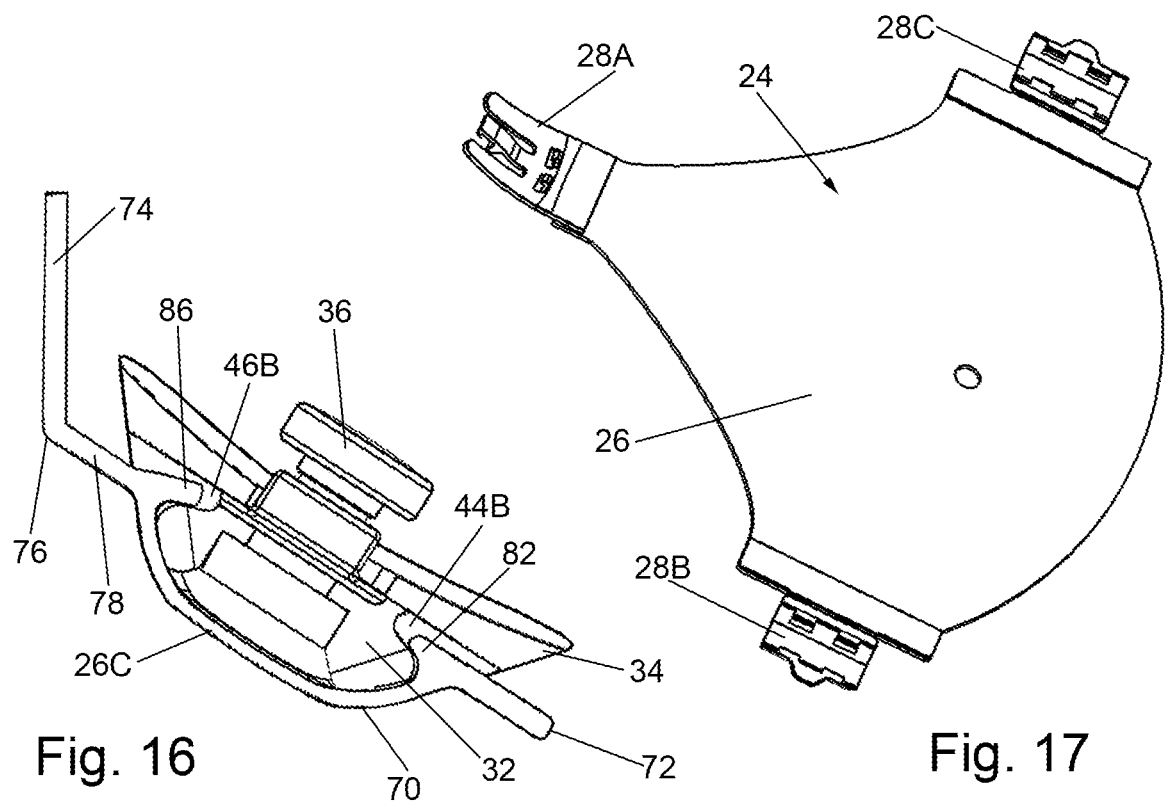

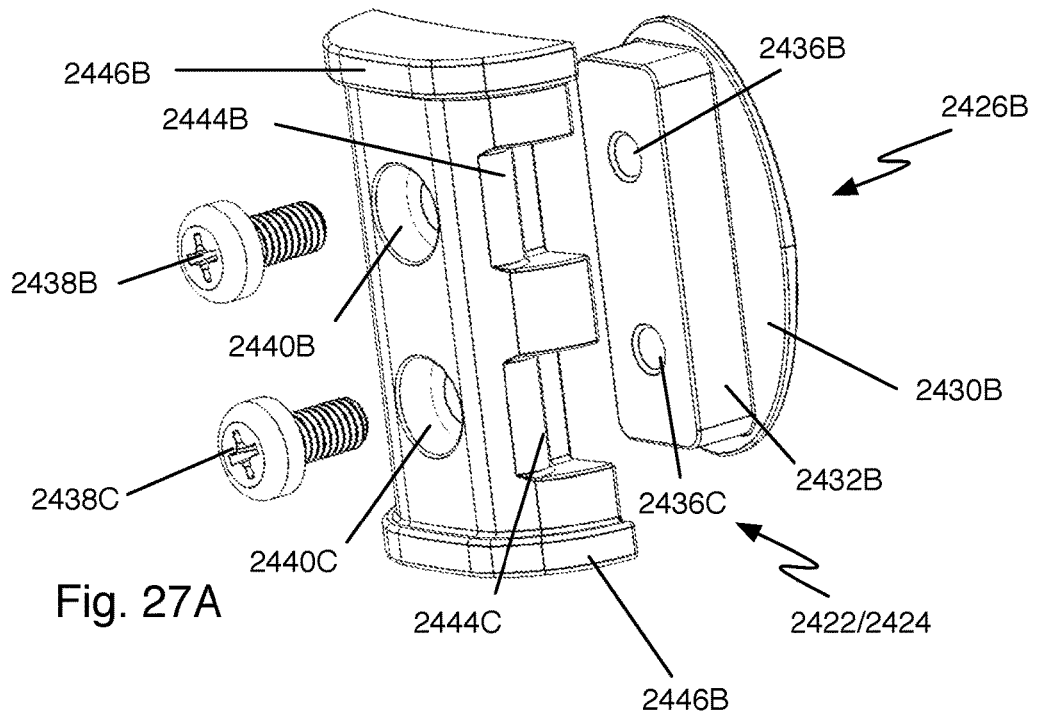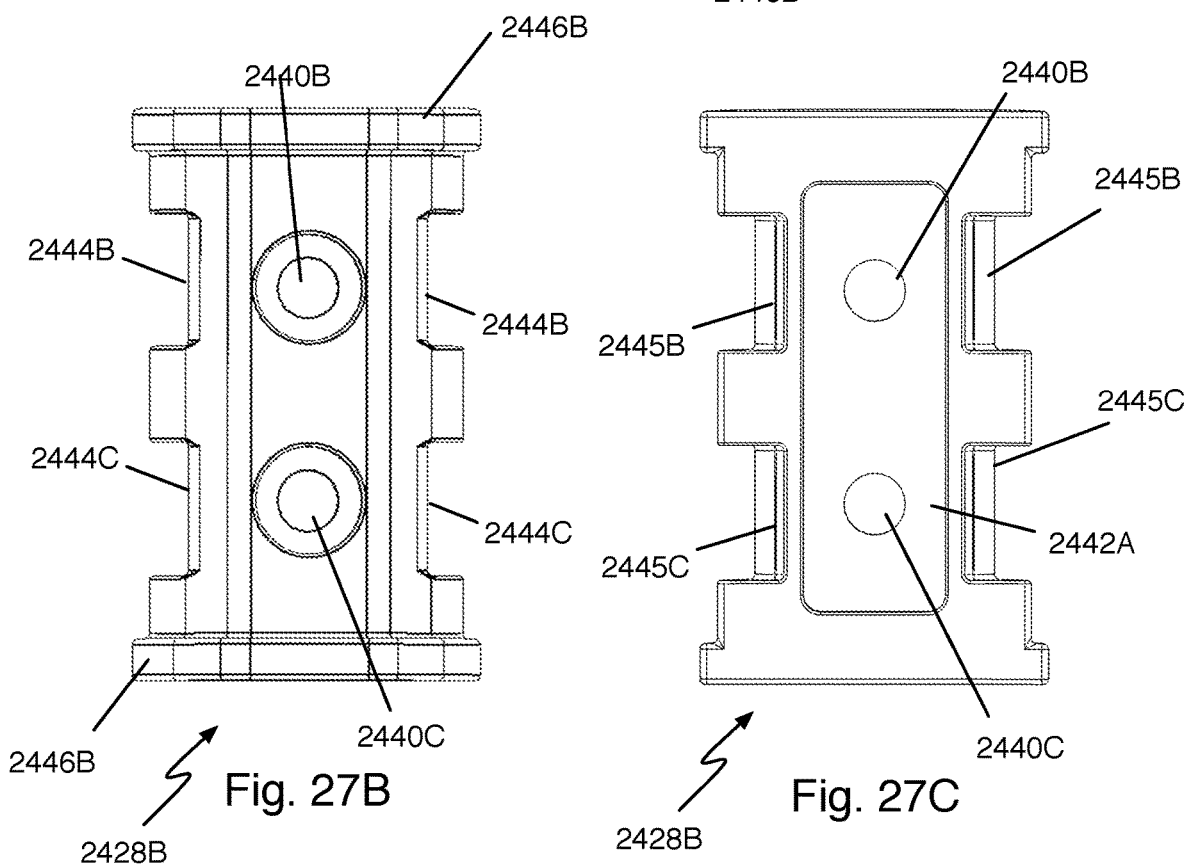

HEAD RESTRAINT SYSTEM

CROSS-REFERENCE TO RELATED APPLICATIONS

This application claims priority under 35 U.S.C. § 119, based on U.S. Provisional Patent Application No. 62/358,327, filed Jul. 5, 2016, the disclosure of which is hereby incorporated by reference herein.

BACKGROUND

Embodiments described herein relate generally to devices for use in radiation therapy and more particularly to a head restraint system for radiation, e.g., proton, therapy.

Patient immobilization is essential for the safety and efficacy of radiation, and particularly, proton, therapy. In particular, patients undergoing proton therapy are typically disposed on a treatment table or couch associated with the proton particle accelerator instrument. Various couch-tops and overlays or other patient support panels are commercially available for disposition on the treatment table, with the patient being disposed on the couch-top/overlay. Fixation or immobilization devices are available for use with the couch-tops/overlays to position the patient in the same anatomic position and location on the treatment table as on the planning table (i.e., the table upon which the radiation treatment plan was established).

One type of immobilizing and positioning device used for treating the head and neck region is the thermoplastic mask. This device is a perforated mask formed of a thermoplastic material or web that is heated and stretched over the head and neck areas (and sometimes portions of the upper torso) while the patient is disposed on the overlay on the planning table, with peripheral portions of the mask being connected to the overlay by clips or other attachment means forming a portion of the mask until the thermoplastic cools and sets. That action results in a mask that is molded to closely conform to the patient's individual anatomy to provide a very secure fit to immobilize the patient's head at a precise desired position for subsequent radiation treatment. Those same clips or other attachment means are then used to releasably secure the mask to respective connectors, brackets or some other means on the overlay or patient support panel on the treatment table when the patient is to be given the radiation treatment to immobilize the patient's head at the position and orientation that was established when the mask was molded.

For proton therapy, it is important that the patient's head be rigidly supported and immobilized in the desired position, while ensuring that the mask is as comfortable as possible. As is known, the thermoplastic material of the mask may tend to shrink somewhat after its initial molding. As a result, when the mask is applied to patient doing the subsequent radiation treatment the fit may not be exactly as initially taken so that the patient's head is not immobilized at the precise position desired and comfort is compromised. Thus, a need exists for a system to ensure that the mask can be adjusted to hold the patient's head at the precise position as when the mask was molded on the patient. The subject invention addresses that need by providing a head restraint system which is adjustable to ensure that the patient's head (and, if desired, head and upper torso) can be repeatedly and comfortably immobilized at a desired position by a thermoplastic mask connected to the patient support panel or overlay on which the patient is disposed.

SUMMARY OF THE INVENTION

In accordance with one aspect of the invention, head restraint device for connecting to a patient support panel for use in a head restraint system is provided. The head restrain device comprises a face mask and at least one clip for securing the face mask to a connector positioned on the patient support panel. The at least one clip comprises a mounting portion configured for securing to an edge of the face mask, an engagement portion projecting from the mounting portion and configured to resiliently engage the connector to secure the at least one clip to the connector, and a release tab projecting from the engagement portion oppositely from the mounting portion. The engagement portion comprises a C-shaped member that includes at least one pair of opposing engagement teeth. In an exemplary embodiment, the at least one pair of opposing engagement teeth are configured to engage corresponding undercut notches in the connector in a snap-on manner. A force applied to the release tab causes at least one of the engagement teeth to deflect to release the engagement portion from the connector.

In an exemplary implementation, the face mask comprises a thermoplastic material configured to be custom formed to a patient prior to use. The head restraint device may further comprise a first clip mounted to a top of the face mask and second and third clips mounted to opposing sides of the face mask. In an exemplary embodiment, the engagement portions of the second and third clips may two pairs of opposing engagement teeth.

In accordance with one aspect of the invention, a patient support panel for a head restraint system is provided. The head restraint system includes the patient support panel and a head restraint assembly. The head restraint assembly comprises a face mask and at least one clip secured to the face mask. The patient support panel comprises a first portion configured to support the upper torso of a patient thereon, and a second portion configured to support the head of the patient thereon. The second portion of the patient support panel comprises at least one connector located adjacent the periphery thereof. In one embodiment, the at least one connector is movable with respect to the second portion of the patient support panel to provide plural selectable attachment points, each of the selectable attachment points is located at a different position with respect to the second portion of the support panel. The at least one connector is configured to releasably receive the at least one clip of the face mask in a snap-on manner.

In accordance with one preferred aspect of the patient support panel of this invention the at least one connector is configured for movement between a first position and a second position, and vice versa. The, first position establishes a first connection point which, if the at least one clip is releasably secured to the first connection point, holds the face mask closer to the second portion of said support panel. The second position establishes a second connection point which, if the at least one clip is releasably secured to the second connection point, holds the face mask further from the second portion of the support panel. The at least one connector is rotatably secured to the second portion of the support panel for rotation about an axis, whereupon the at least one connector can be rotated to the first position and the second position, and vice versa.

In accordance with another preferred aspect of the patient support panel of this invention the at least one connector includes a base member configured to be moved along the axis between a locked position and an unlocked position, and vice versa. The base member has at least a first notch forming the first connection point and at least a second notch forming the second connection point. The base member when in the unlocked position is released from the second portion of the support panel so the base member can be rotated about the axis, and when in the locked position is releasably locked to the second portion of the support panel.

In accordance with another preferred aspect of the patient support panel of this invention the second portion of the support panel includes a central longitudinal axis and the at least one connector comprises a first connector and a second connector. The first connector is located on one side of the central longitudinal axis of the second portion of the support panel. The second connector is located on the opposite side of the central longitudinal axis of the second portion of the support panel. The face mask includes a central longitudinal axis. The at least one clip of the mask comprises a first clip and a second clip, with the first clip being located on one side of the central longitudinal axis of the face mask and the second clip being located on the opposite side of the central longitudinal axis of the face mask. The first connector is configured to be releasably secured to the first clip and the second connector is configured to be releasably secured to the second clip.

In accordance with another aspect of this invention a head restraint system for a patient to be exposed to a radiation beam is provided. The system comprises a support panel and a head restraint assembly. The support panel comprises a first portion configured to support the upper torso of a patient thereon and a second portion configured to support the head of the patient thereon. The second portion of the support panel comprises at least one connector located adjacent the periphery thereof. The at least one connector is movable with respect to the second portion of the support panel to provide plural selectable attachment points, each of the selectable attachment points being located at a different position with respect to the second portion of the support panel. The head restraint assembly comprises a face mask and at least one clip secured to the face mask. The at least one clip is configured for releasable securement to a selected one of the plural attachment points of the at least one connector of the second portion of the support panel.

In accordance with one preferred aspect of the head restraint system of this invention the at least one connector is configured for movement between a first position and a second position, and vice versa. The, first position establishes a first connection point which, if the at least one clip is releasably secured to the first connection point, holds the face mask closer to the second portion of said support panel. The second position establishes a second connection point which, if the at least one clip is releasably secured to the second connection point, holds the face mask further from the second portion of the support panel. The at least one connector is rotatably secured to the second portion of the support panel for rotation about an axis, whereupon the at least one connector can be rotated to the first position and the second position, and vice versa.

In accordance with another preferred aspect of the head restraint system of this invention the at least one connector includes a base member configured to be moved along the axis between a locked position and an unlocked position, and vice versa. The base member has at least a first notch forming the first connection point and at least a second notch forming the second connection point. The base member when in the unlocked position is released from the second portion of the support panel so the base member can be rotated about the axis, and when in the locked position is releasably locked to the second portion of the support panel.

In accordance with another preferred aspect of the head restraint system of this invention the second portion of the support panel includes a central longitudinal axis and the at least one connector comprises a first connector and a second connector. The first connector is located on one side of the central longitudinal axis of the second portion of the support panel. The second connector is located on the opposite side of the central longitudinal axis of the second portion of the support panel. The face mask includes a central longitudinal axis. The at least one clip of the mask comprises a first clip and a second clip, with the first clip being located on one side of the central longitudinal axis of the face mask and the second clip being located on the opposite side of the central longitudinal axis of the face mask. The first connector is configured to be releasably secured to the first clip and the second connector is configured to be releasably secured to the second clip.

In accordance with another aspect of this invention a head restraint assembly for a head restraint system is provided. The head restraint system includes the head restraint assembly and a patient support. The patient support panel has a first portion configured to support the upper torso of a patient thereon and a second portion configured to support the head of the patient thereon and includes at least one connector located adjacent the periphery thereof. The head restraint assembly comprises a face mask, at least one clip and a hinge. The at least one clip is configured for releasable securement to the at least one connector of the second portion of the support panel. The hinge pivotably connects the at least one clip to the face mask.

In accordance with one preferred aspect of the head restraint assembly of this invention the hinge is a living hinge.

In accordance with another preferred aspect of the head restraint assembly of this invention the at least one clip comprises a member configured to be snap-fit to the at least one connector of the support panel.

In accordance with another aspect of this invention a head restraint system for a patient to be exposed to a radiation beam is provided. The system comprises a support panel and a head restraint assembly. The support panel comprises a first portion configured to support the upper torso of a patient thereon and a second portion configured to support the head of the patient thereon. The second portion of the support panel comprises at least one connector located adjacent the periphery thereof. The at least one connector is movable with respect to the second portion of the support panel to provide plural selectable attachment points, each of the selectable attachment points being located at a different position with respect to the second portion of the support panel. The head restraint assembly comprises a face mask, at least one clip, and a hinge. The at least one clip is secured to the face mask by the hinge. The at least one clip is configured for releasable securement to a selected one of the plural attachment points of the at least one connector of the second portion of the support panel.

In accordance with one preferred aspect of the head restraint system of this invention the hinge is a living hinge.

In accordance with another preferred aspect of the head restraint system of this invention the at least one clip comprises a member configured to be snap-fit to the at least one connector of the support panel.

In accordance with another preferred aspect of the head restraint system of this invention the at least one connector is configured for movement between a first position and a second position, and vice versa. The, first position establishes a first connection point which, if the at least one clip is releasably secured to the first connection point, holds the face mask closer to the second portion of said support panel. The second position establishes a second connection point which, if the at least one clip is releasably secured to the second connection point, holds the face mask further from the second portion of the support panel. The at least one connector is rotatably secured to the second portion of the support panel for rotation about an axis, whereupon the at least one connector can be rotated to the first position and the second position, and vice versa.

In accordance with another preferred aspect of the head restraint system of this invention the at least one connector includes a base member configured to be moved along the axis between a locked position and an unlocked position, and vice versa. The base member has at least a first notch forming the first connection point and at least a second notch forming the second connection point. The base member when in the unlocked position is released from the second portion of the support panel so the base member can be rotated about the axis, and when in the locked position is releasably locked to the second portion of the support panel.

In accordance with another preferred aspect of the head restraint system of this invention the second portion of the support panel includes a central longitudinal axis and the at least one connector comprises a first connector and a second connector. The first connector is located on one side of the central longitudinal axis of the second portion of the support panel. The second connector is located on the opposite side of the central longitudinal axis of the second portion of the support panel. The face mask includes a central longitudinal axis. The at least one clip of the mask comprises a first clip and a second clip, with the first clip being located on one side of the central longitudinal axis of the face mask and the second clip being located on the opposite side of the central longitudinal axis of the face mask. The first connector is configured to be releasably secured to the first clip and the second connector is configured to be releasably secured to the second clip.

BRIEF DESCRIPTION OF THE DRAWINGS

FIG. 1 is an isometric view of one exemplary head restraint system according to an embodiment described herein;

FIG. 2 is an enlarged exploded isometric view of a portion of the system shown in FIG. 1;

FIG. 3 is a side elevation view of a portion of the patient support panel or overlay of FIG. 1;

FIG. 4 is an anterior end elevation view of the patient support panel or overlay of FIG. 1;

FIG. 5 is a bottom plan of the portion of the patient support panel or overlay of FIG. 3;

FIG. 9 is an exploded isometric view of the components making up the adjustable connector shown in FIG. 8;

FIG. 10 is another exploded isometric view, taken from a different angle, of the components making up the adjustable connector shown in FIG. 8;

FIG. 11 is an enlarged top plan view of a base component of the adjustable connector show in FIGS. 8-10;

FIG. 12 is a sectional view taken along line 12-12 of FIG. 11;

FIG. 13 is an enlarged isometric view of a portion of the components of the adjustable connector shown in FIGS. 8-10;

FIG. 14 is an anterior end elevation view of the patient support panel or overlay shown with portions, e.g., clips, of the head restraint assembly shown in FIG. 1 releasably secured to two connectors of the patient support panel or overlay in their "low" position or state;

FIG. 15 is an anterior end elevation view of the patient support panel or overlay illustrating two connectors of the patient support panel or overlay in their "high" position or state;

FIG. 16 is a vertical sectional view of a portion of the system shown in FIG. 6, illustrating a clip of the head restraint assembly connected to the connector in its "low" position;

FIG. 17 is a reduced isometric view of the underside of the head restraint assembly shown in FIG. 1 prior to being molded to the face of a patient;

FIGS. 27A-27C are an exploded isometric view, a top view, and a bottom view, respectively, of the lateral connectors of FIGS. 24 and 25;

DETAILED DESCRIPTION OF THE PREFERRED EMBODIMENTS

Figure 6:
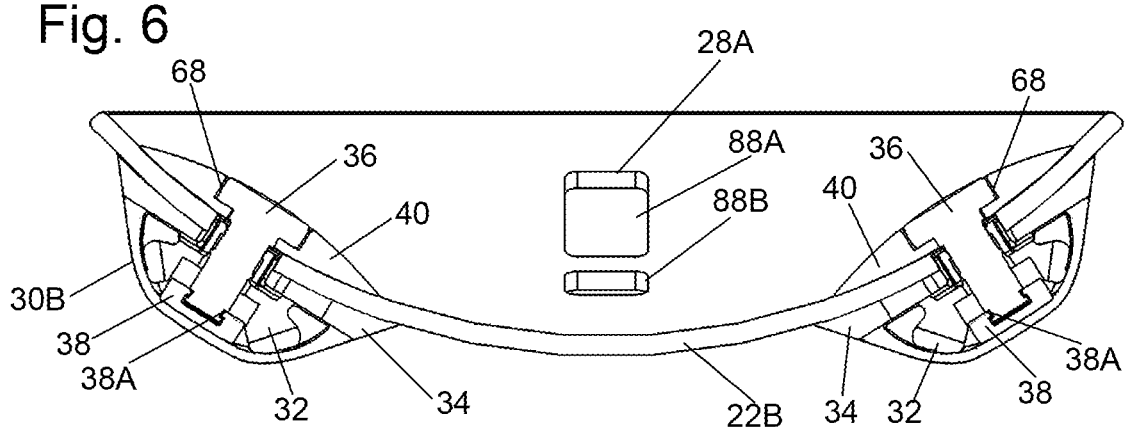
FIG. 6 is an enlarged sectional view taken along line 6-6 of FIG. 5, and illustrating the position of a pair of adjustable connectors of the patient support panel or overlay in their "low" position or state.

Referring now to the various figures of the drawing wherein like reference characters refer to like parts, there is shown in FIG. 1 a system 20 constructed in accordance with embodiments described herein for use in immobilizing the head of a patient during radiation therapy. The system includes a support panel in the form of an overlay 22 and a head restraint device 24.

The overlay 22 is arranged to be disposed on any conventional couch-top (not shown), like those available from CIVCO Medical Products Company or any other manufacturer/supplier of such goods. The couch-top is in turn arranged to be disposed on a cradle and docking station associated with radiation therapy apparatus, e.g., a proton beam generator (not shown). The overlay 22 is sized to accommodate the head, neck and upper torso of a patient, with the remainder of the patient being disposed on the couch-top. To that end, the overlay has a general profile of the shape of the upper portion of a human being and includes a first generally planar portion or section 22A configured to receive the upper torso of the patient and a second concave portion or section 22B configured to receive the head of the patient. The overlay 22 is arranged to be positioned on the couch-top at any desired position thereon, e.g., with the head and neck portion of the overlay 22 extending beyond the forward end of the couch-top. The overlay 22 is formed of any suitable strong and lightweight material. One particularly suitable material is structural foam having a thin carbon fiber external coating or skin. The overlay can be formed of other materials as well, e.g., low density plastics, solid carbon fiber, KEVLAR®, etc.

The head restraint device 24 constitutes one aspect described herein and includes an assembly of a thermoplastic face mask 26 and plural clips 28A, 28B and 28C. The mask 26 is of generally conventional construction in the form of a web or sheet of thermoplastic material having a multitude of apertures therein. The clips are provided to releasably secure the head restraint assembly 24 to the overlay 22. In the exemplary embodiment, the head restraint assembly the clip 28A is axially disposed on the centerline or central longitudinal axis of the face mask adjacent its top (anterior) end, whereas the clips 28B and 28C form lateral or side clips that are disposed on opposite sides of the centerline. Both of the lateral clips 28B and 28C are of identical construction and will be described in detail later. The axial clip 28A is of a different construction than the lateral clips 28B and 28C and will also be described in detail later. The lateral clips are fixedly secured to portions of the periphery of the face mask 26 on opposite sides of the mask. In particular, one clip 28B is fixedly secured to the edge of the face mask on the right side of the face mask, while the other clip 28C is fixedly secured to the edge of the face mask on the left side of the face mask. The axial clip 28A is fixedly secured to the edge of the face mask at the top end of the face mask and on its centerline. The lateral clips 28B and 28C are configured to be releasably secured to respective connectors 30B and 30C of the head-receiving section 22B of the overlay 22. Those connectors are located on the head receiving section adjacent its periphery and on opposite sides of its centerline CL. The axial clip 28A is configured to be releasably secured to an axial connector 30A of the head-receiving section 22B of the overlay 22. The connector 30A is located adjacent the periphery of the head receiving section on the centerline CL.

As mentioned earlier the face mask 26 is formed of a thermoplastic material so that it can be heated to enable it to soften so that it can be stretched over the head and face of a patient, with the clips 28A, 28B and 28C being connected to connectors 30A, 30B and 30C, respectively. Thus, the face mask will conform to the contour of the patient's head and face. When the face mask 26 has cooled the resulting assembly, i.e., the head restraint assembly 24, will be an integral unit that is custom fit to accommodate the patient's head so that it can be repeatedly reconnected to the head-receiving section 22B of the overlay to immobilize the patient's head during subsequent radiation therapy.

Figure 7:
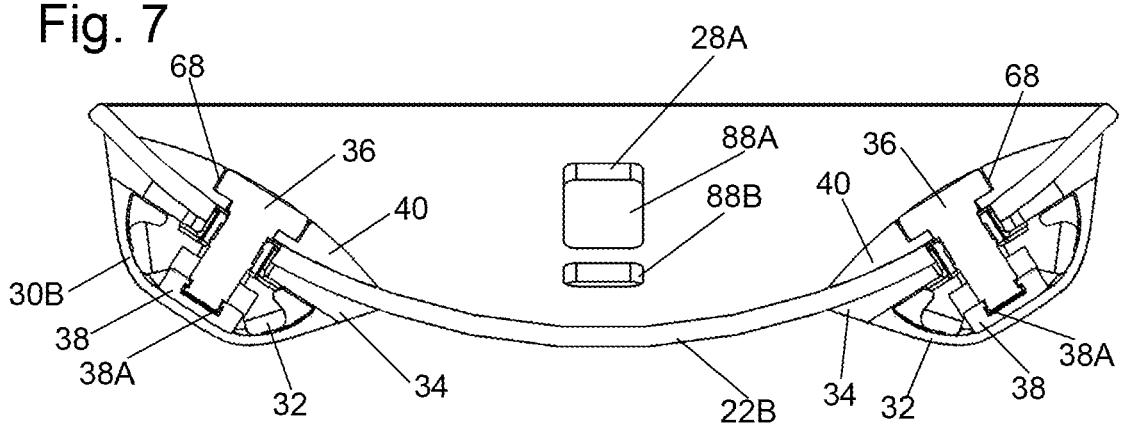
FIG. 7 is an enlarged sectional view taken along line 6-6 of FIG. 5, and illustrating the position of the pair of adjustable connectors of the patient support panel or overlay in their "high" position or state.

As mentioned above, the face mask 26 will likely shrink somewhat after its initial molding. Thus, in order to accommodate this anticipated shrinkage, the connectors 30B and 30C are adjustable so that their position with respect to the head receiving section 22B can be adjusted to different locations below the top of the periphery of the head receiving section. In particular, in the exemplary embodiment the connectors 30B and 30C and be adjusted so that they are in either a "low" position, like shown in FIGS. 6 and 14, or in a "high position" like shown in FIGS. 7 and 15.

The details of the construction and operation of connectors 30B and 30C will be described in additional detail below. When connectors 30B and 30C are in the "low" position they will be located a greater distance below the top of the peripheral edge of the head receiving section 22B than when they are in the "high" position. The connector 30A of the exemplary embodiment is fixed and not adjustable, although it can be made adjustable, if desired.

During the molding of the face mask 26 the clip 28A will be connected to the stationary or fixed position connector 30A, while the clips 28B and 28C will be connected to the connectors 30B and 30C when those connectors are in their "low" position. Thus, should the face mask 26 shrink after its initial molding, when it is used to immobilize the patient's head it can be connected via its clips 28B and 28C to the connectors 30B and 30C, respectively, of the head receiving section when those connectors are set to their "high" position, thereby taking up the mask's shrinkage. As such, the patient's head will be in the same precise location and orientation with respect to the head receiving section as it was when the mask was initially molded on the patient.

Turning now to FIGS. 8-12 the details of the lateral connectors 30B and 30C will now be described. Those two connectors are of identical construction. In the interest of brevity only the details of the left side lateral connector 30C will be described. The connector 30C includes a base member 32, an interface or spacer plate 34, a pivot pin 36, a cap 38, and a mounting plate 40. Each of those members is constructed of a suitable material for use in proton beam therapy so as not to block, excessively attenuate or otherwise degrade the beam.

As best seen in FIG. 11 the base member 32 is an elongated member having a longitudinal central axis or centerline A and a pair of longitudinally extending long sides 44 and 46 extending parallel to the axis A. Each long side includes a pair of notches in the face thereof.

For example, a pair of notches 44A and 44B are located on the side 44, whereas a pair of notches 46A and 46B are located on the side 46. The depth of all of the notches 44A, 44B, 46A and 46B is the same, i.e., the notches 44A and 44B extend inward from the side 44 by the same distance, while the notches 46A and 46B extend inward from the side 46 by the same distance. The top surface 48 of the base member 32 is planar and includes a pair of circular bosses 50 projecting upward therefrom. The bosses are centered on the central longitudinal axis A. A pair of slightly arcuate walls 52 project upward from the top surface 48 and are centered along a longitudinal axis B, which is offset laterally from the central longitudinal axis A. The inner surfaces of the walls 52 establish a circular space therebetween, which circular space is centered on the axis B. Four elongated fingers 54, which are equidistantly spaced from one another, project upward from the top surface 48 within the circular space and are also centered on the axis B. A hole 56 extends through the base member from its bottom surface to the top surface 48 and is centered between the upstanding fingers 54. An annular recess 58 (FIG. 9) extends about the periphery of the hole 56 at the bottom of the base member and includes a conical portion extending to the bottom surface of the base member. The hole 56 is configured to receive the shaft of the pivot pin 36, with the annular recess 58 configured to receive the cap 38. That cap will be described later and is secured to the bottom or free end of the pivot pin 36.

The pivot pin is fixedly secured to the head restraint section 22A by means of the mounting plate 40, as will also be described later. As such the pin extends through a longitudinally extending slot 60 located closely adjacent the left side edge of the head receiving section 22A of the overlay so that the free end of the pin is located below the curved undersurface of the head receiving section 22A for securement to the base member 32. Inasmuch as the undersurface of the head receiving section is arcuate and the top surface of the base member 32 is planar, the heretofore identified spacer plate 34 is provided to fill up the interface between the head receiving section and the base member. The spacer plate 34 includes a member having a concave top surface which is configured to mate with and closely engage the arcuate undersurface of the head receiving section 22B, and a planar bottom surface which is arranged to closely engage the planar top surface of the base member 32. A central elongated slot 62 extends down the centerline of the spacer plate 34 and is configured to receive the upwardly projecting walls 52 and the upwardly projecting fingers 54 of the base member 32. A pair of apertures 64 is located adjacent opposite ends of the slot 60 on the centerline of the plate 34 to receive respective ones of the bosses 50.

The mounting plate 40 is a disk-like, circular member having a lower surface which is configured to mate with the top surface of the head receiving section 22A contiguous with the slot 60. The top surface of the mounting plate is slightly convex and includes a central hole 66 (FIG. 9) through which the shaft of the pivot pin 36 extends. The top portion of the central hole is in the form of an enlarged annular recess 68 (FIG. 10) to accommodate the head of the pivot pin 36. The upper or free end of each of the fingers 54 is in the form of an inwardly directed flange or tab 54A (FIG. 13). The spacing between the free edges of the opposing tabs 54 is equal to the outside diameter of the shaft of the pivot pin 36 so that the shaft can fit into the space between the tabs of the fingers 54. The underside of mounting plate 40 includes a pair of downwardly projecting arcuate walls 40A which are configured to extend through the slot 62 in the spacer plate 34. The inner surface of the arcuate walls 40A are arcuate and spaced apart to fit the arcuate walls 52 of the base member 32 therebetween.

The pivot pin 36 is best seen in FIGS. 6, 7, 9, 10 and 13, and includes a unitary member. The pin includes an enlarged head 36A from which a circular shaft 36B projects. The central longitudinal axis of the pivot pin's shaft forms a rotation axis about which the base member and the spacer plate can be rotated as unit through an arc of 180 degrees to establish either the "high" or "low" position of the connector 30C, as will be described later. An annular ring or flange 36C extends outward about the periphery of the shaft at approximately the midpoint thereof and an annular recess 36D extends inward about the periphery of the shaft closely adjacent the bottom or free end of the shaft. The recess 36D serves as the means for connecting the cap 38 to the bottom of the pivot pin 36.

Figure 8:
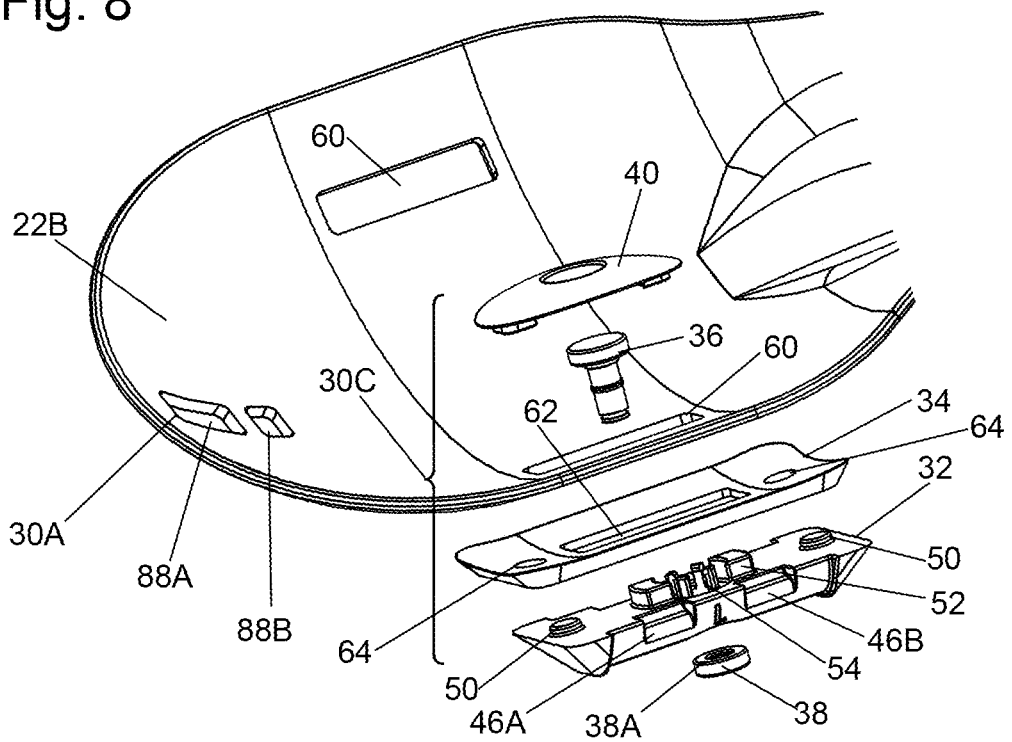
FIG. 8 is an exploded isometric view of the head receiving section of the patient support panel and one of its adjustable connectors.

The cap 38, is best seen in FIGS. 8 and 10, and includes a disk-like member having an undercut circular recess 38A in its upper surface. The periphery of the undercut recess 38A is configured to snap fit into the annular recess 36D of the pivot pin 36 to fixedly secure the cap onto the pivot pin after the free end of the pivot pin has been extended through the opening 56 and the annular recess 58 in the base member 32.

As mentioned above, the base member 32 and the spacer plate 34 are arranged to be rotated as a unit about the longitudinal axis of the pivot pin to configure the connector 30C in either its "high" or "low" state. For example, assuming that the connector 30C had been in its low state, such as used to mold the face mask 24 onto the head of the patient, the long side 46 of the base member will be directed outward. Since the position of the base member and the spacer unit is established by the axis of the fixed pivot pin 36, which is located on the offset axis B of the base member, the notches 46A and 46B will be located closer to the axis of the pivot pin, Accordingly, those notches will be located more remotely, i.e., lower, from the top surface of the periphery of the head receiving section 22B than if the connector was in the high position.

In order to orient the connector 30C so that it is in the "high" position, such as would be the case when the system 20 is used to immobilize the patient's head during radiation, e.g., proton, therapy, all that is required is to push the cap 38 then pull the unit of the base member and spacer plate downward. That action causes the unit of the base member and spacer plate to slide along the shaft of the pivot pin, guided by the inwardly directed tabs 54A until the arcuate walls 52 of the base member 32 are fully removed from the slot 60. Once that has occurred, the concave top surface of the spacer plate will be in the state where it is disengaged or freed from the convex bottom surface of the head receiving section 22B of the overlay, whereupon the unit of the base member and the spacer plate can be rotated 180 degrees about the axis of the pivot pin. The rotation of the unit of the base member and the spacer plate to that orientation brings the long side 44 facing outward. Once the long side 44 is facing outward, the unit of the base member and the spacer plate can be pushed inward along the rotation axis until the concave top surface of the spacer plate engages the convex undersurface of the head restraint section 22B, the head of the pivot pin 36A is then pressed whereupon the connector will now be locked in the "high" position. In that position, the notches 44A and 44B on the long side 44 of the base member 32 will be located closer, e.g., higher, to the top surface of the periphery of the head receiving section 22B than when the connector was in the low position. The connector 30B is operated in the same manner to bring it to the high position.

Once the connectors 30B and 30C are each in their high position, the head restraint assembly can be connected to them. To that end, the clips 28B and 28C of the head restraint assembly are reconnected to the connectors 30B and 30C of the overlay by releasably securing portions of those clips (to be described later) into the respective notches 44B, 44C, 46B and 46C of the now "high" positioned connectors. In particular, as shown in FIG. 15, those notches will be located higher and more outward with respect to the top surface of the periphery of the head receiving section 22B than when the connectors 30B and 30C are in the low position (like shown in FIG. 14).

As best seen in FIGS. 9, 10 and 13, the base member 32 includes indicia in the form of the letter "L" on the long side 46 to indicate the side of the connector which when facing outward establishes the "low" position. Indicia in the form of the letter "H" are provided on the long side 44 of the base member to indicate the high position side, although that indicia cannot be seen in the various figures of the drawing of this application. The inclusion of the indicia "L" and "H", enables users of the system 20 to readily determine if the connectors 30B and 30C are in their "high" or "low" positions by viewing the indicia on the outwardly facing sides of those connectors. In lieu of the indicia "L" and "H", other indicia, e.g. words, colors, etc., may be used to differentiate the low position orientation from the high position orientation.

As noted above when the connectors 30B and 30C are moved from their low position to their high position they are moved vertically upward to be closer to the top surface of the periphery of the head receiving section 22B. In accordance with one exemplary embodiment of this invention the amount of vertical movement of the notches between the low position and the high position is approximately 1.7 millimeters, but that distance is merely exemplary. Moreover, as also mentioned above when the connectors 30B and 30C are moved from the low to the high position, the spacing between the clips 28B and 28C which are connected to those connectors increases. In order to accommodate the change, e.g., increase, in spacing between the clips when the connectors are in the high position, the clips are preferably constructed to include a hinge. The hinge enables those portions of the clip that are fixedly secured to the mask 26 (as will be described later) to pivot with respect to the portions of the clip secured within the notches of the connectors.

Figure 21:
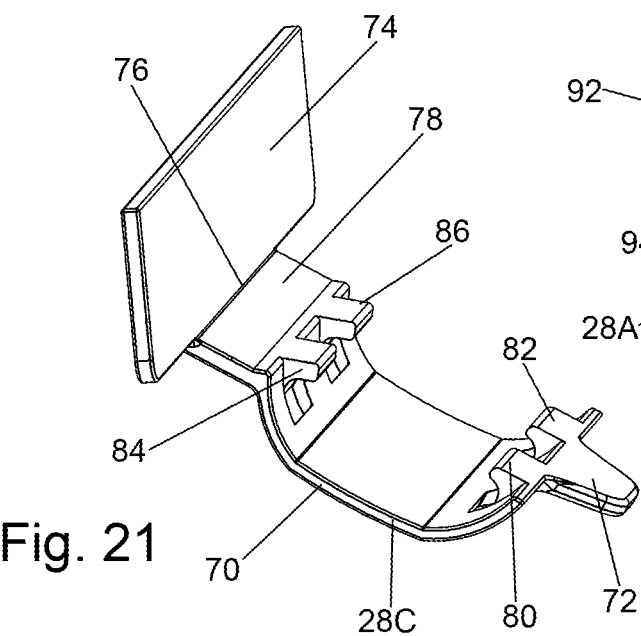
FIG. 21 is an enlarged isometric view of another one of the clip components of the head restraint assembly shown in FIGS. 1, 17 and 18.

Turning now to FIGS. 16 and 21, the details of the construction and operation of the clips 28B and 28C will now be discussed. Clips 28B and 28C are of identical construction. Thus, in the interest of brevity only the details of the construction and operation of the clip 28C will be described. That clip is an integral unit formed of any suitable material, e.g., the material used for the components of the connectors 30B and 30C and includes a generally C-shaped member 70. The outer or free end of the member 70 is in the form of a handle or tab 72. The inner end of the member 70 is in the form of a mounting flange 74, which is a generally planar, and in this exemplary embodiment of rectangular shape. The mounting flange serves as the means for fixedly securing the left side edge portion 26C (FIG. 2) of the mask 26 to the clip 28C. In a similar manner, the right side edge portion 26B (FIG. 2) of the mask is fixedly secured to the mounting flange 74 of the clip 28B. The anterior edge portion 26A (FIG. 2) of the mask is fixedly secured to a mounting area (to be described later) of the clip 28A.

A living hinge 76 interconnects the mounting flange 74 of the clip 28C to a bridging section 78 extending outward from the opposite side of the C-shaped portion 70 as the tab 72. The living hinge 76 enables the mounting flange to pivot with respect to the remainder of the clip. This feature enables the mask to be closely conformed to the patient's anatomy and minimizes any air gaps between the portion 26C of the mask that is connected to the mounting flange, irrespective of whether the connector 30C is in the "low" or "high" state and also accommodates the change in spacing between the mounting flange 74 of the clip 28C and the mounting flange 74 of the clip 28B when those clips are connected to the connectors 30C and 30B, respectively, in either the "low" or "high" positions. It should be noted that while the hinge 76 is preferred to be a living hinge, since that simplifies construction of the clip, the hinge may be of other types, so long as it enables the mounting flange 74 to pivot with respect to the C-shaped portion 70 of the clip.

In order to releasably secure the clip 28C to the connector 30C, the clip includes two pairs of projections for receipt in respective ones of the notches in the connector 30C. In particular, a pair of projections 80 and 82 project inward into the interior space of the C-shaped portion 70 from the location of the tab 72. A pair of similar projections 84 and 86 project inward into the interior space of the C-shaped portion 70 from the location of the bridging section 78. The C-shaped member is configured to be flexed open by pressing upon its tab 72, to enable the projections to snap-fit into respective notches in the connector 30C, depending upon whether the connector is in the "low" position or the "high" position. In particular, when the connector is in the low position, like shown in FIG. 16, the C-shaped portion 30 will be flexed open to enable the projections 80 and 82 to snap-fit into the notches 44A and 44B, respectively, while the projections 84 and 86 snap-fit into the notches 46A and 46B, respectively, thereby releasably securing the clip 28C to the connector 30C. Conversely, when the connector is in the high position, the C-shaped portion 30 will be flexed open to enable the projections 80 and 82 to snap-fit into the notches 46A and 46B, respectively, while the projections 84 and 86 snap-fit into the notches 44A and 44B, respectively, thereby releasably securing the clip 28C to the connector 30C. Irrespective of which position the connector 30 is in, the clip 28C can be released from its connection to that connector, by merely pressing downward on the tab 72 to flex the C-shaped portion 70 open, and thereby release the projections 80-86 from their respective notches.

Figure 19:
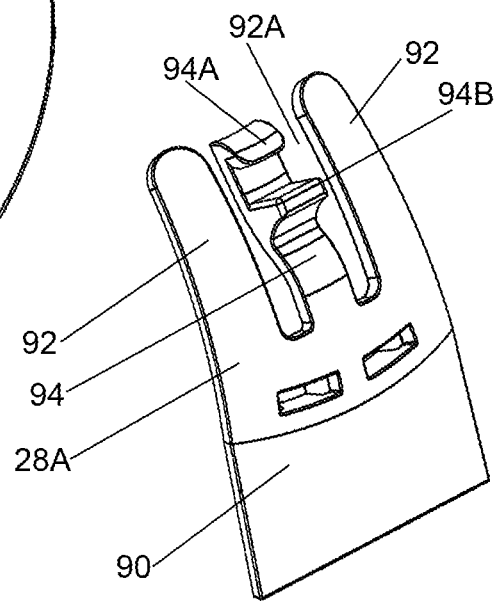
FIG. 19 is an enlarged isometric view of one of the clip components of the head restraint assembly shown in FIGS. 1, 17 and 18.
Figure 20:
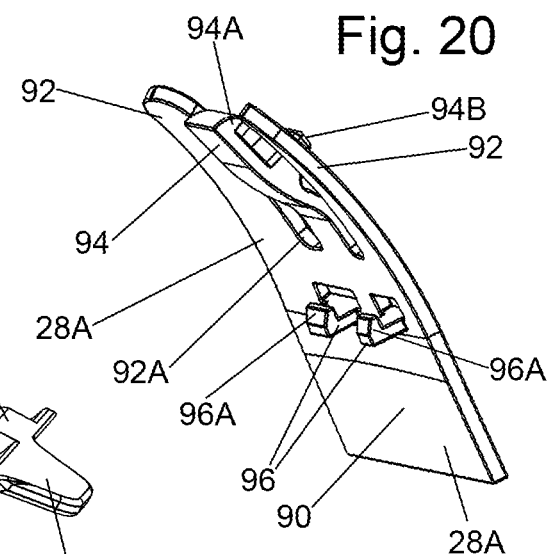
FIG. 20 is an enlarged isometric view similar to FIG. 19, but showing the clip taken from a different angle.

Turning now to FIGS. 19 and 20, the details of the axially located clip 28A will now be described. That clip is configured to be releasably secured to the connector 30A of the head restraint section 22B. Before describing the details of the construction and operation of the clip 28A, a description of the construction of the connector 30A is in order. To that end, as can be seen in FIGS. 4-8 the connector 30A includes a square opening 88A extending through the head restraint section 22B from the top surface thereof to the bottom surface thereof. Located closely below the opening 88A is a rectangular slot 88B extending through the head restraint section 22B from the top surface thereof to the bottom surface thereof. The axial clip 28A includes a unitary member, preferably formed of the same material as that of the lateral clips 28B and 28C, and is a somewhat elongated, slightly arcuate shaped member. Its inner end 90 is generally planar and serves as the heretofore mentioned mounting flange of the clip 28A to which the anterior edge portion 26A (FIG. 2) of the mask is fixedly secured. The opposite or free end 92 of the clip 28A includes a recess 92A in which a finger 94 projects. As best in in FIG. 20, the finger 94 is offset slightly under the plane of the free end portion 92. A small ear 92A projects upward from the free end of the finger 94. A larger ear 94B projects upward from approximately the middle portion of the finger 94 and is taller than the ear 94A. The finger 94 is configured to be flexed about its base, i.e., the portion at which the finger joins the remainder of the clip. A pair of short height fingers 96 project downward from the underside of the clip adjacent the mounting flange 90. Each finger 96 terminates in an outwardly projecting tab 96A. Each of the fingers 96 is configured to be flexed about its base, i.e., the portion at which the finger joins the remainder of the clip.

The clip 28A is configured so that it can be releasably secured to the connector 30A in a snap on or push on manner. To achieve that end, the clip is juxtaposed confronting to the head restraint section 22B at the location of the connector 30A and the free end of the clip is moved into engagement with the slot 88A of the head restraint section at that location, whereupon the finger 94 flexes so that its ear 94A snap-fits within the square hole 88B from the inside of the head restraint section 22B, while the free end portions 92 on opposite sides of the recess 92A overlie the contiguous outer surface of the head restraint section 22B. At the same time the fingers 96 hook over the periphery of the head restraint section 22B to hold the clip in place without the need for a separate fastening element.

The clip 28A can be released from its connection to the connector 30A, by merely pressing on the tab 94B, to free the ear 94A from the portions of the head restraint section 22B contiguous with the slot 88B, whereupon the clip 28A can be manipulated free from the opening 88A. The clip can then be removed from the head restraint section 22B.

Figure 18:
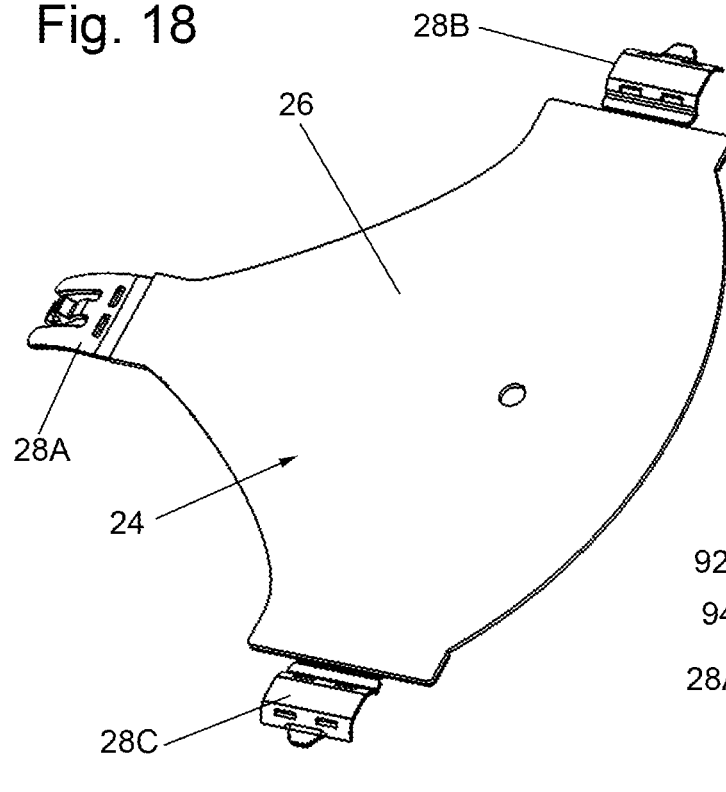
FIG. 18 is an alternative isometric view of the head restraint assembly of FIG. 1 illustrating the bottom side of the head restraint assembly prior to being molded to the face of a patient.
Figure 22:
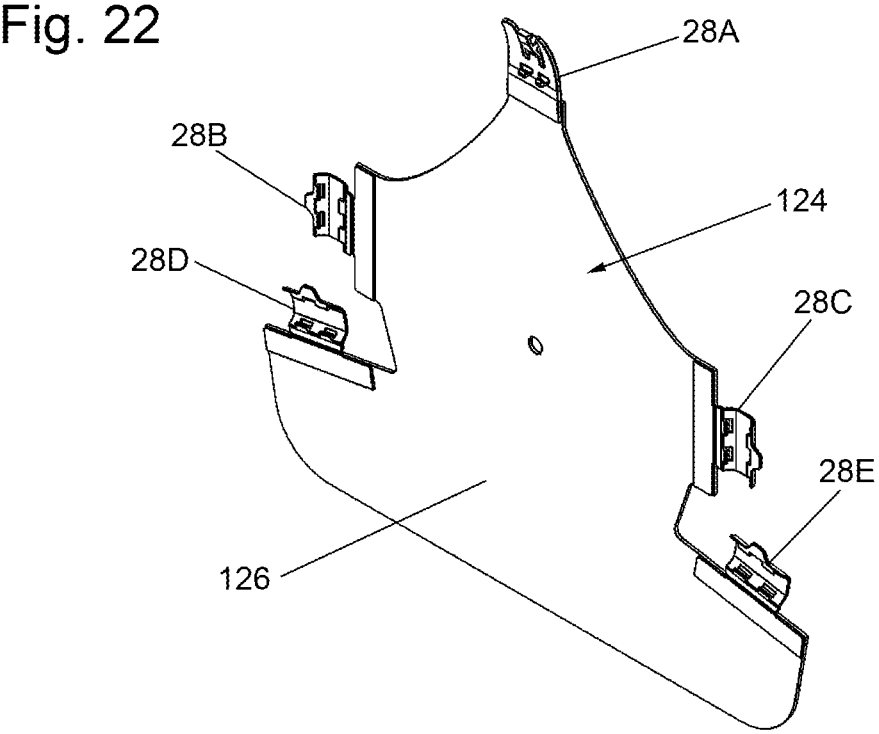
FIG. 22 is an isometric view illustrating an alternative head restraint assembly configured to be connected to the overlay at five connection points.

It should be noted that the head restraint system described heretofore is of a three point connection configuration (as most clearly shown in FIGS. 17 and 18), wherein it is connected to the patient support panel 22 by three connectors 30A, 30B and 30C. However, that is merely only one embodiment of a head restraint assembly of this invention. Thus, FIG. 22, there is shown a head restraint assembly 124, which is configured for five point connection to the patient support panel or overlay 22. To that end, the overlay 22 includes a pair of connectors 30D and 30E which are located in the shoulder area of the portion 22A of the overlay. The head restraint assembly 124 is similar in construction to the head restraint assembly 24, except that its mask 126 includes two additional portions with associated clips 28D and 28E for connection to the shoulder-located connectors 30D and 30E. In the interest of brevity, the common components of the head restraint assemblies 24 and 124 will be given the same reference numbers and the details of their construction and operation will not be reiterated. Moreover, the multitude of apertures that are in the face mask 26 are found in the face mask 126, but have been omitted from FIG. 22 in the interest of drawing simplicity. In fact, those apertures have been omitted from FIGS. 17 and 18 for the same reason. The clips 28D and 28E of the head restraint assembly are of identical construction to the clips 28B and 28C of the head restraint assembly 24. Similarly, the connectors 30D and 30E of the overlay portion 22A are of identical construction to the connectors 30B and 30C of the head support portion 22B of the overlay.

Figure 23:
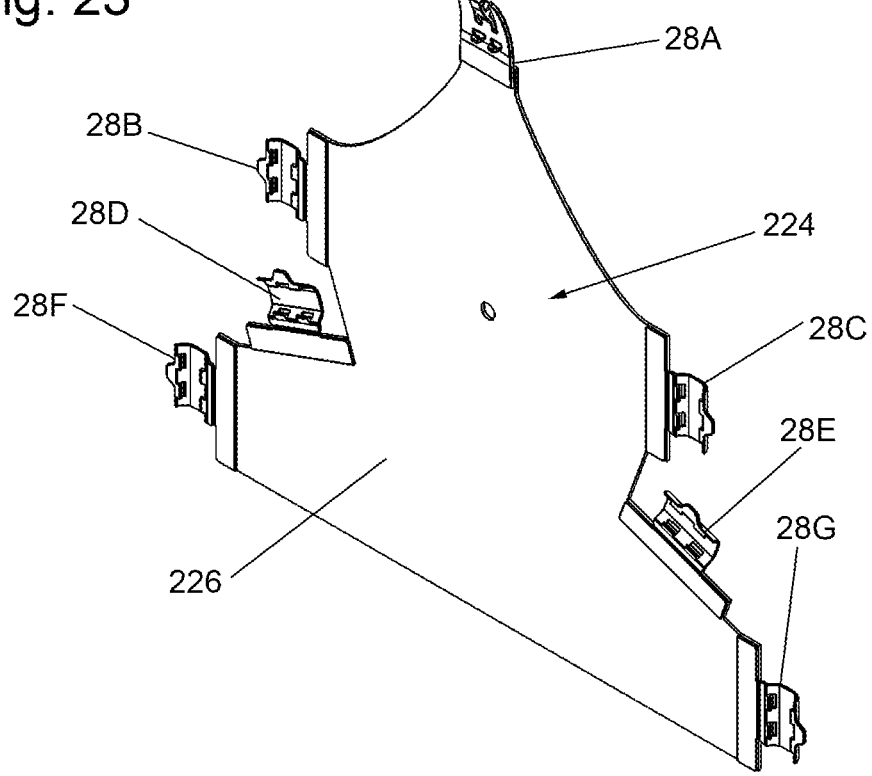
FIG. 23 is an isometric view illustrating another alternative head restraint assembly configured to be connected to the overlay at seven connection points.

In FIG. 23, there is shown a head restraint assembly 224, which is configured for seven point connection to the patient support panel or overlay 22. To that end, the overlay 22 also includes a pair of connectors 30F and 30G which are located posteriorly of the shoulder area of the portion 22A of the overlay. The head restraint assembly 224 is similar in construction to the head restraint assembly 124, except that its mask 226 includes two additional portions with associated clips 28F and 28G for connection to the connectors 30F and 30G. In the interest of brevity, the common components of the head restraint assemblies 24, 124 and 224 will be given the same reference numbers and the details of their construction and operation will not be reiterated. Moreover, the multitude of apertures that are in the face mask 26 are found in the face mask 226, but have been omitted from FIG. 23 in the interest of drawing simplicity.

The clips 28F and 28G of the head restraint assembly 224 are of identical construction to the clips 28B and 28C of the head restraint assembly 24. Similarly, the connectors 30F and 30G of the overlay portion 22A are of identical construction to the connectors 30B and 30C of the head receiving section 22B of the overlay.

As should be appreciated from the foregoing, the adjustable thermoplastic attachment points of described herein accommodate and account for mask shrinkage. Thus, the subject invention provides a viable and effective means of attaching a thermoplastic mask to a patient positioning platform or overlay. Moreover, the living hinge which interconnects the clip to the thermoplastic face mask results in a mask that is more easily conformed to the patient anatomy (e.g., it minimizes air gaps between the portion of the thermoplastic that is attached to the clip and the patient).

The exemplary head restraint system described above are merely exemplary of various systems that can be constructed in accordance with embodiments described herein. For example, it is contemplated that the overlay connectors can be configured to establish more than the two positions, e.g., a "low," "high," and "intermediate" position (the "intermediate position being between the low and high positions). In such a modified system, the base member would be constructed so that its rotation brings at least one notch (or other connection point for the associated clip of the mask) that is located the furthest distance from the rotation axis to face outward. That configuration would establish the "high" position. Rotation of the base member about the rotation axis to bring at least one other notch (or other connection point for the associated clip of the mask) that is located closest to the rotation to face outward would establish the "low" position. Rotation of the base member about the rotation axis to bring at least one other notch that is located at an intermediate distance between the at least one notch establishing the "low" position and the at least one notch establishing the "high" position to face outward would establish the "intermediate" position. In fact, if desired, more than three positions can be established by appropriate configuration of the base member. Moreover, while the above description makes use of a pivot pin to effect the rotation of the base member, other structures can be used to enable the base member to be rotated to the different positions.

Figure 24:
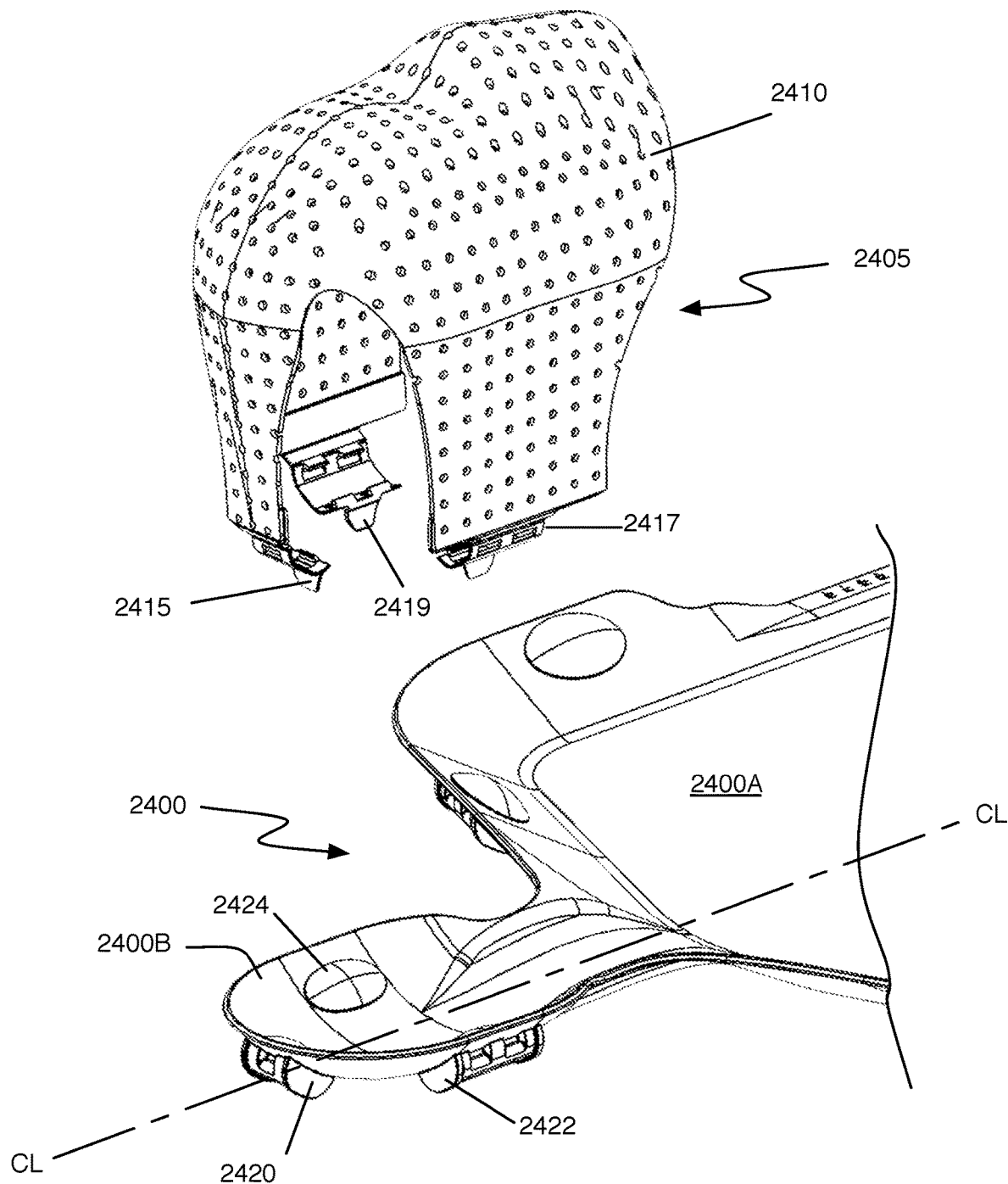
FIG. 24 is an exploded isometric view of a portion of an overlay and a head restraint device consistent with embodiments described herein.

Consistent with embodiments described herein, connectors 30B and 30C may be formed as fixed or non-adjustable attachment points. FIG. 24 is an exploded isometric view of a portion of an overlay 2400 and a head restraint device 2405 consistent with such an embodiment. Similar to overlay 22, described above, overlay 2400 is arranged to be disposed on any conventional couch-top (not shown) and is sized to accommodate the head, neck and upper torso of a patient, with the remainder of the patient being disposed on the couch-top and includes a first generally planar portion or section 2400A configured to receive the upper torso of the patient and a second concave portion or section 2400B configured to receive the head of the patient.

Head restraint device 2405 constitutes one aspect described herein and includes a face mask 2410 and a number of clips 2415, 2417, and 2419. Face mask 2410, similar to face mask 26 described above, may be formed of a web or sheet of thermoplastic material having a multitude of apertures therein, which may be custom formed to a patient's head prior to an initial treatment session. As described herein, clips 2415, 2417, and 2419 are configured to releasably secure head restraint assembly 2405 to the overlay 2400 via corresponding fixed position connectors 2420, 2422, and 2424. In some implementations, each of clips 2415-2419 and connectors 2420-2424 may be formed in a substantially similar manner, such as that described below in relation to clips 2417 and 2149 and connectors 2422 and 2424. In other implementations, such as shown in FIG. 24, clips 2415-2419 and connectors 2420-2424 may have different configurations based on position on head restraint device 2405.

For example, in one embodiment, anterior clip 2415, which is positioned on the centerline or central longitudinal axis (denoted as line CL in FIG. 24) on an anterior surface of face mask 2410, may be formed differently from lateral clips 2417 and 2419 that are disposed on opposite sides of the centerline. In the embodiment of FIG. 24, each of lateral clips 2417 and 2419 are of identical construction, although such a configuration is not necessary.

Lateral clips 2417/2419 are fixedly secured to portions of the periphery of the face mask 2410 on opposite sides of the mask, via one or more fasteners, an adhesive, etc. In particular, clip 2417 is fixedly secured to the edge of the face mask 2410 on the right side, while the clip 2419 is fixedly secured to the edge of the face mask on the left side. Lateral clips 2417 and 2419 are configured to be releasably secured to respective connectors 2422 and 2424 of overlay 2400. Those connectors are located on overlay 2400 adjacent its periphery and on opposite sides of its centerline CL. Anterior clip 2415 is configured to be releasably secured to anterior connector 2420 of overlay 2400. Anterior connector 2420 is located adjacent the periphery of the head receiving section 2400B on the centerline CL.

Figure 25:
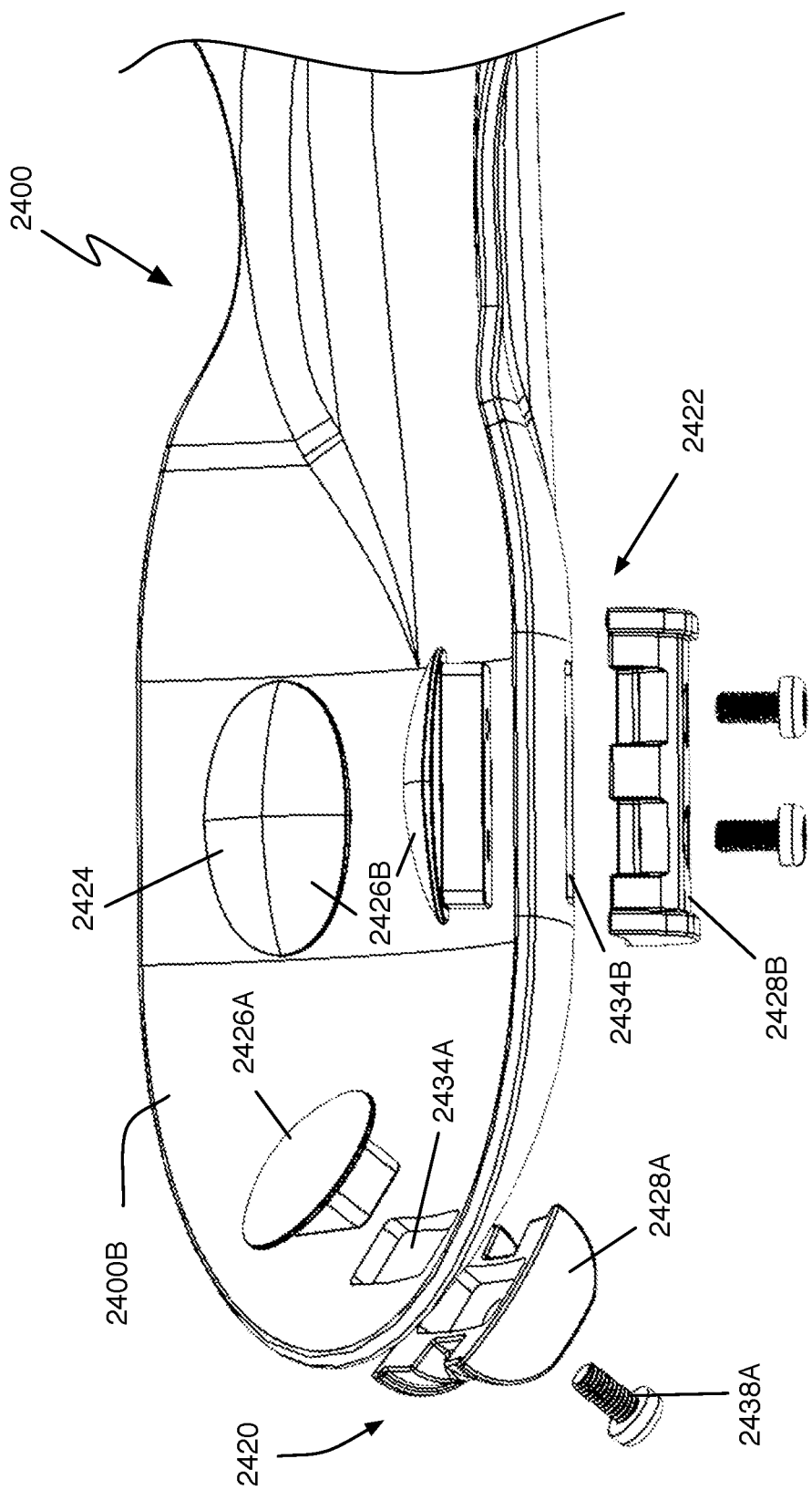
FIG. 25 is an exploded isometric view of the head receiving section of FIG. 24.
Figure 26A:
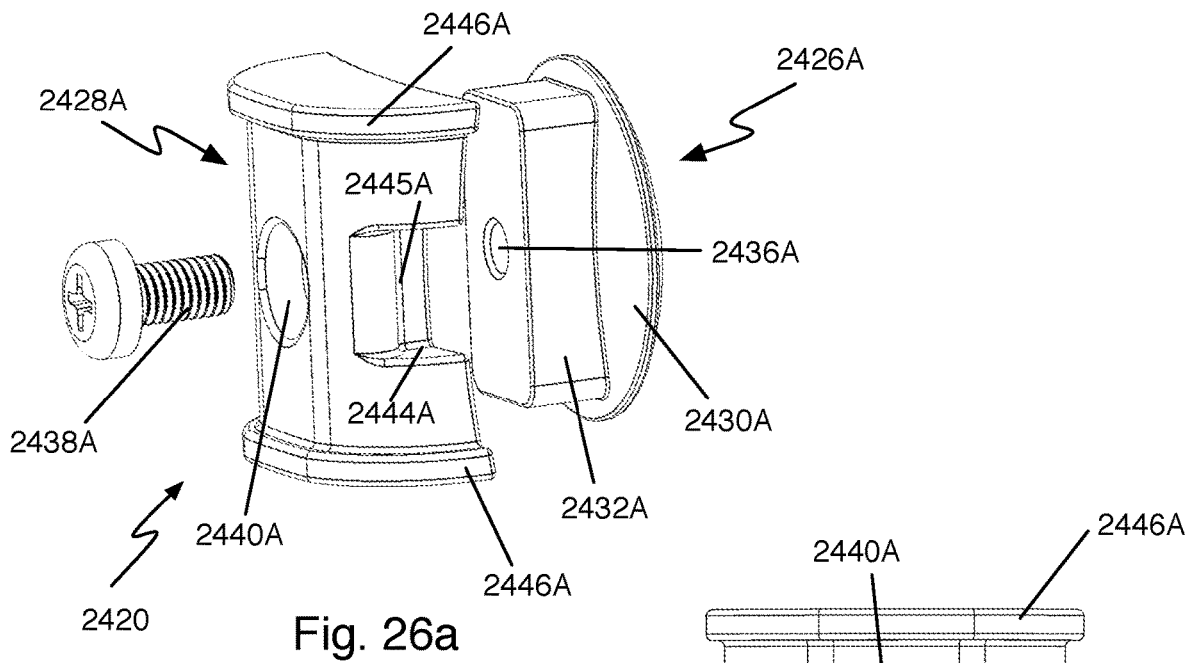
FIGS. 26A-26C are an exploded isometric view, a top view, and a bottom view, respectively, of the anterior connector of FIGS. 24 and 25.
Figure 26B:
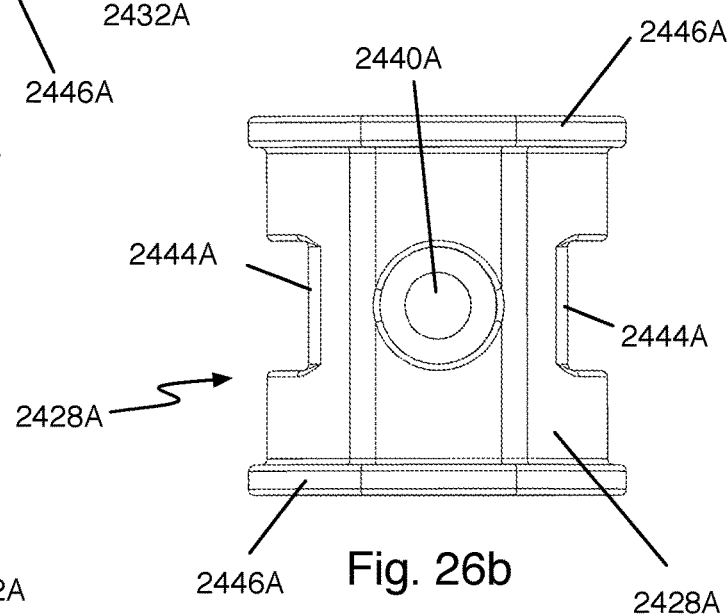
Figure 26C:
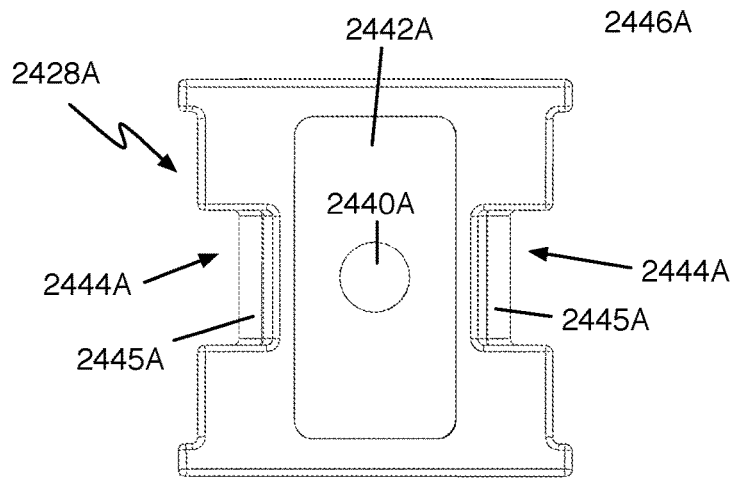

FIG. 25 is an exploded isometric view of head receiving section 2400B of overlay 2400 and illustrates the construction and manner of assembly of connectors 2420-2424. FIGS. 26A, 26B, and 26C, are an exploded isometric view, a top view, and a bottom view, respectively, of anterior connector 2420. FIG. 27A, 27B, and 27C are an exploded isometric view, a top view, and a bottom view, respectively, of one of lateral connectors 2422/2424.

As shown in FIGS. 25 and 26A, anterior connector 2420 includes a mounting element 2426A and a clip fastening element 2428A. Mounting element 2426A includes a substantially disk-like, circular member 2430A having a lower surface configured to mate with the top surface of the overlay 2400 upon assembly. A generally rectangular connecting portion 2432A projects from the lower surface of mounting element 2426A and is configured for receipt within a correspondingly shaped aperture 2434A in overlay 2400, as shown in FIG. 25. As shown in FIG. 26a, connecting portion 2432A may include a threaded (e.g., jacketed) opening 2436A for receiving a connecting bolt 2438A or other fastening element during assembly over overlay 2400.

Clip fastening element 2428A includes a generally planar elongated member configured to securely engage clip 2415 during use. Clip fastening element 2428A includes an aperture 2440A formed therethrough for receiving bolt 2438A during assembly to secure clip fastening element to overlay 2400. More specifically, as shown in FIG. 26A, aperture 2440A may include a shoulder portion for engaging a head of bolt 2438A. As shown in FIG. 26C, an undersurface of clip fastening element 2428A includes a generally rectangular cavity 2442A sized to receive at least a portion (e.g., a tip) of connecting portion 2432A of mounting element 2426A after it passes through aperture 2434A. As shown in FIG. 26A, an upper surface of clip fastening element 2428A includes a generally arcuate configuration that includes a pair of opposing notches 2444A configured to engage anterior clip 2415, as described in additional detail below. As shown in FIGS. 26A and 26C, each of notches 2444A may include undercut portions 2445A for engaging one or more clip projections or teeth, as described in additional detail below.

Furthermore, as shown in FIGS. 26A and 26B, the upper surface of clip fastening element 2428A may further include a pair of opposing ridges 2446A formed on the edges of clip fastening element 2428A in a direction perpendicular or transverse to clip fastening element 2428A's longitudinal axis. Ridges 2446A are configured to project above the upper surface of clip fastening element 2428A and serve to decrease a likelihood that clip 2415 slips off of clip fastening element 2428A during connection.

Regarding lateral connectors 2422 and 2424, as shown in FIGS. 25 and 27A, each of lateral connectors 2422 and 2424 includes a mounting element 2426B and a clip fastening element 2428B. Mounting element 2426B, similar to mounting element 2426A described above, includes a substantially disk-like, circular member 2430B having a lower surface configured to mate with the lateral portions of the top surface of overlay 2400 upon assembly. A generally rectangular connecting portion 2432B projects from the lower surface of mounting elements 2426B and is configured for receipt within correspondingly shaped apertures 2434B in overlay 2400, as shown in FIG. 25 (only one of which is shown). In contrast to anterior connector 2415 described above, the configuration of lateral connectors 2422 and 2424 may be wider than connector 2420 in a longitudinal direction to provide a broader coupling force on sides of face mask 2410 to more securely limit side to side patient movement during a procedure. Consequently, rather than having a singular threaded opening, as in anterior connector 2415, connecting portion 2432B of lateral connectors 2422 and 2424 may include two (or more) threaded openings 2436B and 2436C for receiving connecting bolts 2438B and 2438C or other fastening elements during assembly of overlay 2400.

Clip fastening element 2428B includes a generally planar elongated member configured to securely engage clip 2417/2419 during use. Clip fastening element 2428B of lateral connector 2422/2424 includes an apertures 2440B and 2440C formed therethrough for receiving bolts 2438B and 2438C during assembly to secure clip fastening element 2428B to overlay 2400. More specifically, as shown in FIG. 27B, apertures 2440B/2440C may include shoulder portions for engaging a head of bolts 2438B/2438C. Similar to clip fastening element 2428A, an undersurface of clip fastening element 2428B includes a generally rectangular cavity (not shown) sized to receive at least a portion (e.g., a tip) of connecting portion 2432B of mounting element 2426B after it passes through aperture 2434B in overlay 2400. As shown in FIG. 27A, an upper surface of clip fastening element 2428B includes a generally arcuate configuration that includes two pairs of opposing notches 2444B and 2444C configured to engage lateral clips 2417/2419, as described in additional detail below. As shown in FIGS. 27A and 27C, each of notches 2444B/2444C includes undercut portions 2445B/2445C for engaging one or more clip projections or teeth, as described in additional detail below. Furthermore, as shown in FIGS. 27A and 27B, upper surface of clip fastening element 2428B may further include a pair of opposing ridges 2446B on edges of clip fastening element 2428B that are perpendicular to notches 2444B.

Figure 28:
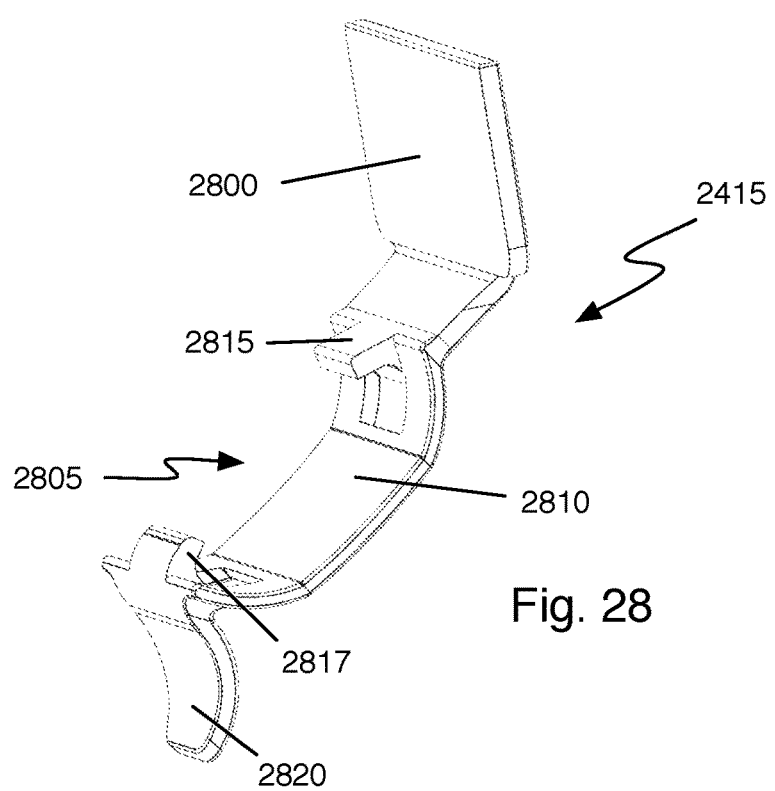
FIG. 28 is an isometric view of the anterior clip of FIG. 24 consistent with embodiments described herein.
Figure 29:
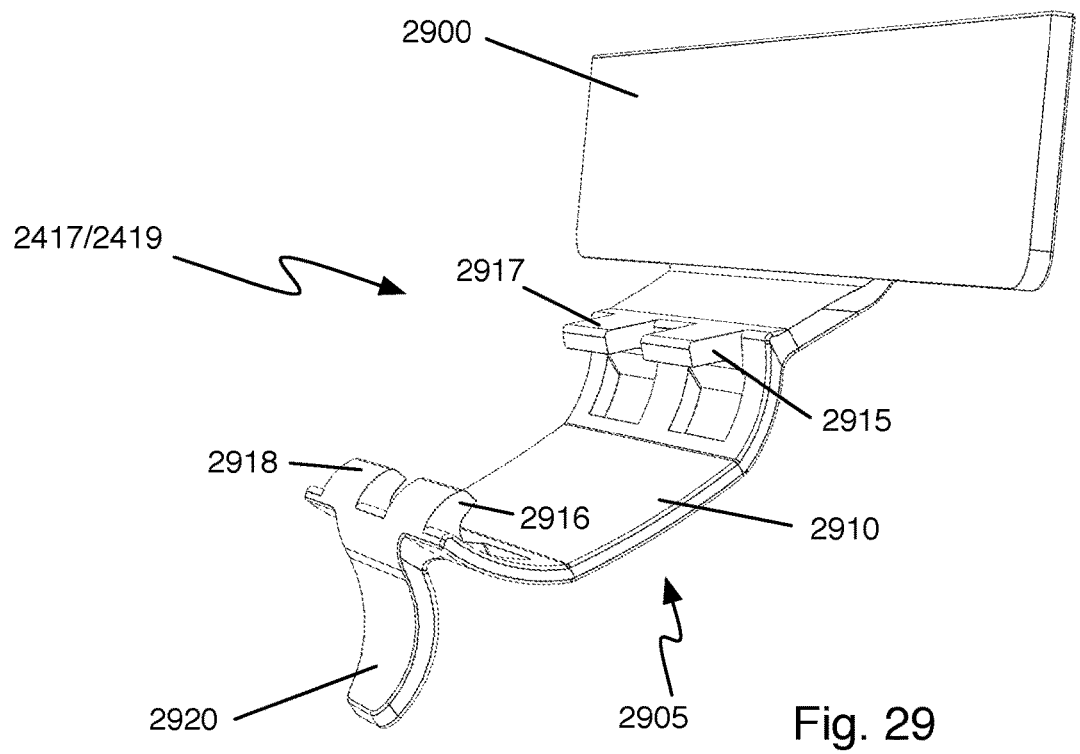
FIG. 29 is an isometric view of the lateral clip of FIG. 24 consistent with embodiments described herein.
Figure 30A:
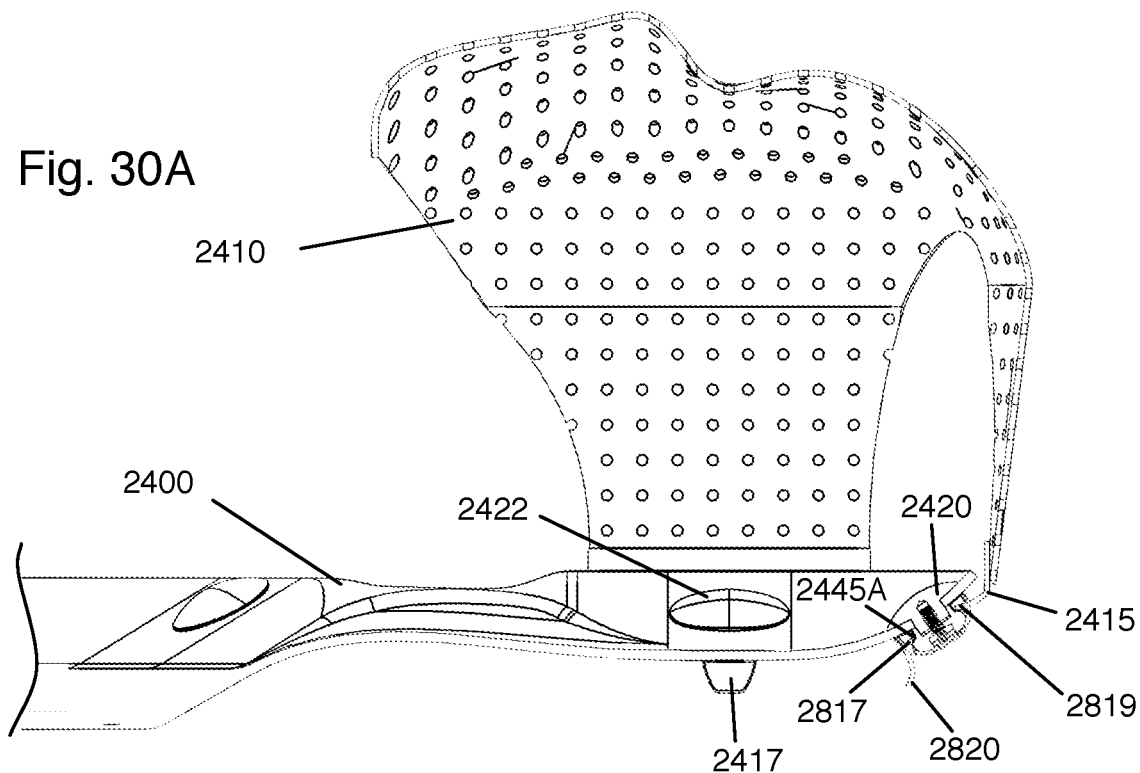
FIGS. 30A and 30B are cross-sectional and rear isometric views, respectively, of portions of the overlay and head restraint device of FIG. 24 in an assembled configuration.
Figure 30B:
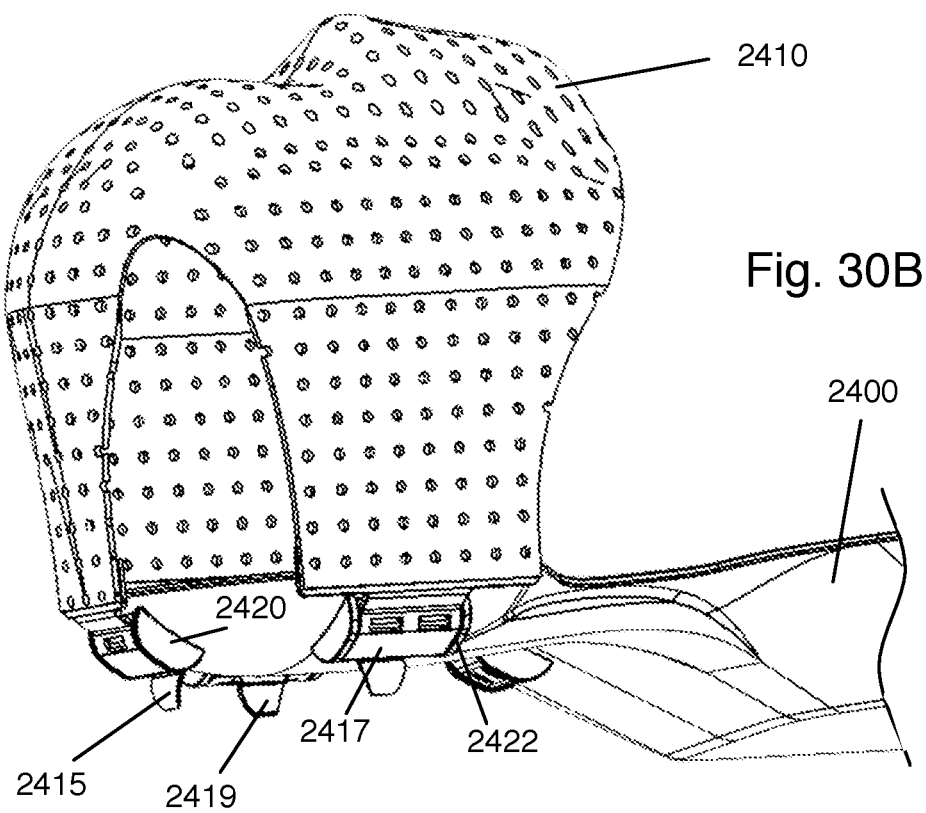

FIG. 28 is an isometric view of anterior clip 2415 and FIG. 29 is an isometric view of lateral clip 2417/2419 consistent with embodiments described herein. FIGS. 30A and 30B are cross-sectional (along the centerline CL in FIG.

24) and rear isometric views, respectively, of portions of overlay 2400 and head restraint device 2405 in an assembled configuration.

As shown in FIG. 28, anterior clip 2415 is configured to be releasably secured to the anterior connector 2420 of head restraint section 2405. Anterior clip 2415 includes a unitary member preferably formed of a rigid yet resilient material (e.g., a plastic, etc.) and that includes a mounting portion 2800 and an engagement portion 2805. Mounting portion 2800 includes a generally planar configuration and serves as a mounting flange for securing clip 2415 to an anterior edge portion of face mask 2410. Engagement portion 2805 of the clip 2415 includes a generally C-shaped member 2810 projecting from mounting portion 2800. A pair of engagement teeth 2815/2817 project inwardly from the ends of C-shaped member 2810 and toward each other. In some implementations, as shown in FIG. 28, openings or apertures may be formed in C-shaped member adjacent teeth 2815/2817. A release tab 2820 projects rearwardly from the end of C-shaped member 2810 opposite from mounting portion 2800.

As shown in FIGS. 30A and 30B, during securing of face mask 2410 to overlay 2400, C-shaped member 2810 of clip 2415 is pushed onto the upper surface of clip fastening element 2428A causing engagement teeth 2815/2817 to deflect outwardly until clip 2415 advances forwardly such that engagement teeth 2815/2817 are resiliently and clampingly received within notches 2444A and engage undercut portions 2445A, e.g., in a snap-on or push-on manner. To effect removal of clip 2415, a rearward force is exerted on release tab 2820 (e.g., by a technician, doctor, etc.) causing engagement tooth 2817 to deflect or move away from engagement tooth 2815, thus increasing a spacing between teeth 2815/2817 and allowing clip 2415 to be removed from undercut portions 2445A of notches 2444A in fastening element 2428A.

As shown in FIG. 29, lateral clips 2417/2419 are similarly configured to be releasably secured to lateral connectors 2422/2424 of head restraint section 2405. Each lateral clip 2417/2419 includes a unitary member preferably formed of a rigid yet resilient material (e.g., a plastic, etc.) and that includes a mounting portion 2900 and an engagement portion 2905. Mounting portion 2900 includes a generally planar configuration and serves as a mounting flange for securing lateral clips 2417/2419 to a lateral edge portions of face mask 2410. Engagement portion 2905 of the clips 2417/2419 includes a generally C-shaped member 2910 projecting from mounting portion 2900. In contrast with anterior clip 2415, C-shaped member 2910 of clips 2417/2419 includes two pairs longitudinally spaced opposing engagement teeth 2915/2916 and 2917/2918 that project inwardly from the ends of C-shaped member 2810 and toward each other. In some implementations, as shown in FIG. 29, openings or apertures may be formed in C-shaped member adjacent teeth 2915/2916 and 2917/2918. A release tab 2920 projects rearwardly from the end of C-shaped member 2910 opposite from mounting portion 2900.

As shown in FIGS. 30A and 30B, during securing of face mask 2410 to overlay 2400, C-shaped member 2910 of clips 2417/2419 is pushed onto the upper surface of clip fastening element 2428B such that engagement teeth 2915-2918 are resiliently and clampingly received within notches 2444B/2444C and secured against undercut portions 2445B/2445C. To effect removal of clips 2417/2419, a rearward force is exerted on release tab 2920 (e.g., by a technician, doctor, etc.) causing engagement teeth 2916/2918 to deflect or move away from teeth 2915/2917, thus increasing a spacing between teeth 2915-2918 and allowing clip 2417/2419 to be removed from notches 2444B/2444C in fastening element 2428B.

In some embodiments consistent with aspects described herein, mounting portions 2800/2900 and engagement portions 2805/2905 may be joined by a flexible living hinge portion or another type of discretely hinged structure, thus allowing engagement portions 2805/2905 to rotate toward and away from connector 2415 relative to mounting portions 2800/2900 during securing and unsecuring of face mask 2410. However, in other embodiments, a fixed structural relationship between mounting portions 2800/2900 and engagement portions 2805/2905 may be provided.

The above-described head restraint system provides an efficient mechanism for quickly securing a head restraint face mask to a couchtop overlay in a manner that does not require tools or additional fastening components (e.g., screws, pins, etc.). While the use of a hinge forming a portion of at least one clip of the head restraint assembly is described above, it is contemplated that some embodiments need not include any hinge, living or otherwise. Moreover, the face mask may be configured so that it includes only two lateral clips, without any axial clip, or more than two lateral clips without an axial clip. In such a case the head receiving section will need to include appropriate adjustable connectors to releasably secure the clips thereto.

The foregoing description of exemplary implementations provides illustration and description, but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise. Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. A head restraint device for connecting to a patient support panel for use in a head restraint system, comprising:
   a face mask; and
   at least one clip for securing the face mask to a connector positioned on the patient support panel,
   wherein the at least one clip comprises:
      a mounting portion configured for securing to an edge of the face mask;

an engagement portion projecting from the mounting portion and configured to resiliently engage the connector to secure the at least one clip to the connector, wherein the engagement portion comprises a C-shaped member that includes at least one pair of opposing engagement teeth, each of which project inwardly from respective portions of the C-shaped clip; and a release tab projecting from an end of the C-shaped member opposite from the mounting portion, wherein the release tab projects rearwardly from the end of the C-shaped member substantially oppositely from at least one of the engagement teeth, and wherein a force applied to the release tab causes at least one of the engagement teeth to deflect to release the engagement portion from the connector.

2. The head restraint device of claim 1, wherein the at least one clip further comprises a first clip mounted to a top of the face mask and second and third clips mounted to opposing sides of the face mask.

3. The head restraint device of claim 2, wherein the engagement portions of the second and third clips comprise two pairs of opposing engagement teeth.

4. The head restraint device of claim 1, wherein the mounting portion and the engagement portion are joined by a hinge portion.

5. The head restraint device of claim 4, wherein the hinge portion comprises a living hinge.

6. The head restraint device of claim 1, wherein the face mask comprises a thermoplastic material configured to be custom formed to a patient prior to use.

7. The head restraint device of claim 1, wherein the at least one pair of opposing engagement teeth are configured to engage corresponding undercut notches in the connector in a snap-on manner.

8. A support panel for use in head restraint system for a patient to be exposed to a radiation beam, the head restraint system including a head restraint assembly comprising a face mask and at least one clip secured to the face mask, said support panel comprising:

a first portion configured to support the upper torso of a patient thereon; and a second portion configured to support the head of the patient thereon, said second portion of said support panel comprising at least one connector located adjacent the periphery thereof, wherein the at least one connector is movable with respect to said second portion of said support panel to provide plural selectable attachment points, each of said selectable attachment points being located at a different position with respect to said second portion of said support panel, and wherein the at least one connector is configured to releasably receive the at least one clip of the face mask in a snap-on manner.

9. The support panel of claim 8, wherein said at least one connector is configured for movement between a first position and a second position, and vice versa, said first position establishing a first connection point which if the at least one clip is releasably secured to said first connection point holds the face mask closer to said second portion of said support panel, said second position establishing a second connection point which if the at least one clip is releasably secured to said second connection point holds the face mask further from said second portion of said support panel.

10. The support panel of claim 9, wherein said at least one connector is rotatably secured to said second portion of said support panel for rotation about an axis, such that said at least one connector can be selectively rotated between said first position and said second position.

11. The support panel of claim 10, wherein said at least one connector includes a base member configured to be moved along said axis between a locked position and an unlocked position, and vice versa, said base member having at least a first notch forming said first connection point and at least a second notch forming said second connection point, said base member when in said unlocked position being released from said second portion of said support panel so that said base member can be rotated about said axis, said base member, when in said locked position, being releasably locked to said second portion of said support panel.

12. The support panel of claim 11, wherein said at least one connector comprises a pivot pin located at a fixed position with respect to said second portion of said support panel, said pivot pin establishing said axis, and wherein said base member is configured for releasable securement to said pivot pin to enable said base member to be rotated about said axis and to enable said base member to be slid from said locked position to said unlocked position and vice versa.

13. The support panel of claim 8, further comprising a first connector positioned at a top of the second portion and second and third connectors mounted to opposing sides of the second portion.

14. A head restraint system, comprising:

a support panel comprising:

a first portion configured to support the upper torso of a patient thereon; and a second portion configured to support the head of the patient thereon, said second portion of said support panel comprising at least one connector located adjacent the periphery thereof and a head restraint assembly comprising:

a face mask; and at least one clip for securing the face mask to a connector positioned on the support panel, wherein the at least one connector of the second portion of the support panel is configured to releasably receive the at least one clip of the face mask in a snap-on manner, wherein the at least one clip comprises:

a mounting portion configured for securing to an edge of the face mask;

an engagement portion projecting from the mounting portion and configured to resiliently engage the connector to secure the at least one clip to the connector, wherein the engagement portion comprises a C-shaped member that includes at least one pair of opposing engagement teeth, each of which project inwardly from respective portions of the C-shaped clip; and a release tab projecting from an end of the C-shaped member opposite from the mounting portion, wherein the release tab projects rearwardly from the end of the C-shaped member substantially oppositely from at least one of the engagement teeth, wherein a force applied to the release tab causes at least one of the engagement teeth to deflect to release the engagement portion from the connector.

15. The head restraint system of claim 14, wherein said at least one connector is configured for movement between a first position and a second position, and vice versa, said first position establishing a first connection point which if said at least one clip is releasably secured to said first connection point holds said face mask closer to said second portion of said support panel, said second position establishing a second connection point which if said at least one clip is releasably secured to said second connection point holds said face mask further from said second portion of said support panel.

16. The head restraint system of claim 15, wherein said at least one connector is rotatably secured to said second portion of said support panel for rotation about an axis, whereupon said at least one connector can be selectively brought to said first position and said second position, and vice versa.

17. The head restraint system of claim 14, further comprising a first clip mounted to a top of the face mask and second and third clips mounted to opposing sides of the face mask, and wherein the engagement portions of the second and third clips comprise two pairs of opposing engagement teeth.

18. The support panel of claim 8, wherein the at least one connector comprises:

a mounting element; and a clip fastening element, wherein the mounting element includes a connecting portion configured to project through an aperture in the second portion, wherein the clip fastening element is secured to the connecting portion of the mounting element when positioned on the second portion of the support panel, wherein the clip fastening element comprises a planar elongated member having a pair of undercut notches formed on longitudinal edges thereof, wherein the undercut notches are configured to engage corresponding portions of the at least one clip to secure the at least one clip to the clip fastening element.

19. The support panel of claim 18, wherein the clip fastening element of the at least one connector comprises a pair of ridges formed on transverse edges of the planar elongated member.

* * * * *